(12) United States Patent
Steinke et al.

(10) Patent No.: US 12,070,603 B2
(45) Date of Patent: Aug. 27, 2024

(54) NEURAL FEEDBACK ASSISTED DBS

(71) Applicant: Boston Scientific Neuromodulation Corporation, Valencia, CA (US)

(72) Inventors: G. Karl Steinke, Valencia, CA (US); Hemant Bokil, Cambridge, MA (US); Joseph Costello, Ann Arbor, MI (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 218 days.

(21) Appl. No.: 17/650,492

(22) Filed: Feb. 9, 2022

(65) Prior Publication Data
US 2022/0266022 A1    Aug. 25, 2022

Related U.S. Application Data

(60) Provisional application No. 63/148,740, filed on Feb. 12, 2021.

(51) Int. Cl.
*A61N 1/00* (2006.01)
*A61N 1/05* (2006.01)
*A61N 1/36* (2006.01)

(52) U.S. Cl.
CPC ....... *A61N 1/36125* (2013.01); *A61N 1/0553* (2013.01); *A61N 1/3614* (2017.08); *A61N 1/36185* (2013.01)

(58) Field of Classification Search
None
See application file for complete search history.

(56) References Cited

U.S. PATENT DOCUMENTS

| 6,052,624 A | 4/2000 | Mann |
| 6,181,969 B1 | 1/2001 | Gord |

(Continued)

FOREIGN PATENT DOCUMENTS

| AU | 2014351064 | 7/2019 |
| AU | 2019216650 A1 | 9/2019 |

(Continued)

OTHER PUBLICATIONS

International Search Report and Written Opinion regarding corresponding PCT Application No. PCT/US2022/070590, mailed May 30, 2022.

(Continued)

*Primary Examiner* — John R Downey
*Assistant Examiner* — Anant A Gupta
(74) *Attorney, Agent, or Firm* — Lewis & Reese, PLLC

(57) ABSTRACT

Methods and systems for using sensed evoked neural responses for informing aspects of neurostimulation therapy are disclosed. Electrical signals may be recorded during the provision of electrical stimulation to a patient's neural tissue. The electrical signals may be processed and analyzed using one or more classification criteria to determine if the electrical signals contain a neural response of interest. Examples of such neural responses include evoked neural responses that are oscillatory and/or resonant in nature. If the electrical signals include such responses of interest, one or more features may be extracted from the signals and used as biomarkers for informing aspects of neurostimulation therapy, such as directing lead placement, optimizing stimulation parameters, closed-loop feedback control of stimulation, and the like. Various methods and systems described herein are particularly relevant in the context of multi-site stimulation paradigms, such as coordinated reset neuromodulation.

20 Claims, 13 Drawing Sheets

(56) References Cited

U.S. PATENT DOCUMENTS

| | | |
|---|---|---|
| 6,393,325 B1 | 5/2002 | Mann et al. |
| 6,490,486 B1 | 12/2002 | Bradley |
| 6,609,032 B1 | 8/2003 | Woods et al. |
| 6,845,267 B2 | 1/2005 | Harrison et al. |
| 6,909,917 B2 | 6/2005 | Woods et al. |
| 6,950,707 B2 | 9/2005 | Whitehurst |
| 7,555,346 B1 | 6/2009 | Woods et al. |
| 7,582,062 B2 | 9/2009 | Magill et al. |
| 7,930,030 B2 | 4/2011 | Woods et al. |
| 8,121,701 B2 | 2/2012 | Woods et al. |
| 8,180,601 B2 | 5/2012 | Butson et al. |
| 8,265,762 B2 | 9/2012 | Woods et al. |
| 8,401,658 B2 | 3/2013 | Woods et al. |
| 8,606,362 B2 | 12/2013 | He et al. |
| 8,620,436 B2 | 12/2013 | Parramon et al. |
| 8,805,524 B2 | 8/2014 | Woods et al. |
| 8,812,124 B2 | 8/2014 | Lee |
| 8,855,773 B2 | 10/2014 | Kokones et al. |
| 8,868,193 B2 | 10/2014 | Ranu et al. |
| 8,868,196 B2 | 10/2014 | Lee et al. |
| 8,868,197 B2 | 10/2014 | Lee |
| 8,909,350 B2 | 12/2014 | Lee |
| 8,914,119 B2 | 12/2014 | Wu et al. |
| 8,958,615 B2 | 2/2015 | Blum et al. |
| 9,014,820 B2 | 4/2015 | Lee et al. |
| 9,050,473 B2 | 6/2015 | Woods et al. |
| 9,072,905 B2 | 7/2015 | Kokones et al. |
| 9,205,261 B2 | 12/2015 | Kim et al. |
| 9,248,280 B2 | 2/2016 | Moffitt et al. |
| 9,381,356 B2 | 7/2016 | Parker et al. |
| 9,387,328 B2 | 7/2016 | Lee |
| 9,387,334 B2 | 7/2016 | Lee et al. |
| 9,411,935 B2 | 8/2016 | Moffitt et al. |
| 9,511,231 B1 | 12/2016 | Kent et al. |
| 10,183,167 B2 | 1/2019 | Steinke et al. |
| 10,183,168 B2 | 1/2019 | Baru et al. |
| 10,195,439 B2 | 2/2019 | Steinke et al. |
| 10,207,113 B2 | 2/2019 | Lee et al. |
| 10,207,114 B2 | 2/2019 | Lee |
| 10,249,041 B2 | 4/2019 | Varkuti |
| 10,252,059 B2 | 4/2019 | Steinke et al. |
| 10,286,205 B2 | 5/2019 | Steinke et al. |
| 10,406,368 B2 | 9/2019 | Hershey et al. |
| 10,463,860 B2 | 11/2019 | Sinclair et al. |
| 10,549,097 B2 | 2/2020 | Zhang et al. |
| 10,576,292 B2 | 3/2020 | Orinski |
| 10,974,051 B2 | 4/2021 | Steinke et al. |
| 10,994,131 B2 | 5/2021 | Durand et al. |
| 11,020,004 B2 | 6/2021 | Varkuti |
| 11,123,563 B2 | 9/2021 | Mustakos et al. |
| 11,195,609 B2 | 12/2021 | Mustakos et al. |
| 11,344,732 B2 | 5/2022 | Moffitt et al. |
| 11,376,433 B2 | 7/2022 | Zhang et al. |
| 11,478,633 B2 | 10/2022 | Tinkhauser et al. |
| 2005/0065427 A1 | 3/2005 | Magill et al. |
| 2006/0224222 A1 | 10/2006 | Bradley et al. |
| 2007/0244407 A1 | 10/2007 | Osorio |
| 2009/0118786 A1 | 5/2009 | Meadows et al. |
| 2009/0118787 A1 | 5/2009 | Moffitt et al. |
| 2009/0299421 A1* | 12/2009 | Sawchuk .................. A61N 1/37 607/28 |
| 2010/0305660 A1 | 12/2010 | Hegi et al. |
| 2011/0105939 A1* | 5/2011 | Yong .................... A61B 5/7264 600/554 |
| 2012/0046712 A1 | 2/2012 | Woods et al. |
| 2012/0092031 A1 | 4/2012 | Shi et al. |
| 2012/0095519 A1 | 4/2012 | Parramon et al. |
| 2012/0095529 A1 | 4/2012 | Parramon et al. |
| 2013/0289665 A1 | 10/2013 | Marnfeldt et al. |
| 2014/0163639 A1 | 6/2014 | Zhu |
| 2014/0243926 A1* | 8/2014 | Carcieri ............. A61N 1/36071 607/46 |
| 2014/0277282 A1 | 9/2014 | Jaax |
| 2014/0378941 A1 | 12/2014 | Su et al. |
| 2015/0039048 A1 | 2/2015 | Woods et al. |
| 2015/0080982 A1 | 3/2015 | Funderburk |
| 2015/0088228 A1 | 3/2015 | Moffitt |
| 2015/0157861 A1 | 6/2015 | Aghassian |
| 2015/0231402 A1 | 8/2015 | Aghassian |
| 2015/0360033 A1 | 12/2015 | Koubeissi et al. |
| 2015/0360038 A1 | 12/2015 | Zottola et al. |
| 2016/0045747 A1 | 2/2016 | Jiang et al. |
| 2016/0287126 A1 | 10/2016 | Parker et al. |
| 2016/0339251 A1 | 11/2016 | Kent et al. |
| 2016/0361542 A1 | 12/2016 | Kaula et al. |
| 2017/0120056 A1 | 5/2017 | Woods et al. |
| 2017/0189687 A1 | 7/2017 | Steinke et al. |
| 2017/0189689 A1 | 7/2017 | Steinke et al. |
| 2017/0281959 A1 | 10/2017 | Serrano Carmona et al. |
| 2017/0296823 A1* | 10/2017 | Hershey .................. A61N 1/00 |
| 2017/0333701 A1 | 11/2017 | Bradley et al. |
| 2017/0333715 A1 | 11/2017 | De Ridder |
| 2018/0071513 A1 | 3/2018 | Weiss et al. |
| 2018/0071520 A1 | 3/2018 | Weerakoon et al. |
| 2018/0071527 A1 | 3/2018 | Feldman et al. |
| 2018/0110987 A1 | 4/2018 | Parker |
| 2018/0132747 A1 | 5/2018 | Parker et al. |
| 2018/0133459 A1 | 5/2018 | Parker et al. |
| 2018/0140831 A1 | 5/2018 | Feldman et al. |
| 2018/0140843 A1 | 5/2018 | Kent et al. |
| 2018/0221644 A1 | 8/2018 | Grill et al. |
| 2019/0030323 A1 | 1/2019 | Koka et al. |
| 2019/0038902 A1 | 2/2019 | Kaemmerer et al. |
| 2019/0070418 A1 | 3/2019 | Hincapie Ordonez et al. |
| 2019/0076645 A1 | 3/2019 | Bower et al. |
| 2019/0083796 A1 | 3/2019 | Weerakoon et al. |
| 2019/0099602 A1 | 4/2019 | Esteller et al. |
| 2019/0143120 A1* | 5/2019 | Sinclair ............. A61N 1/36067 607/45 |
| 2019/0175915 A1 | 6/2019 | Brill et al. |
| 2019/0209844 A1 | 7/2019 | Esteller et al. |
| 2019/0209851 A1 | 7/2019 | Kothandaraman et al. |
| 2019/0232062 A1 | 8/2019 | Falowski |
| 2019/0262609 A1 | 8/2019 | Brill et al. |
| 2019/0274637 A1 | 9/2019 | Wilson et al. |
| 2019/0275331 A1 | 9/2019 | Zhu |
| 2019/0299006 A1 | 10/2019 | Marnfeldt |
| 2019/0366094 A1* | 12/2019 | Esteller ................ A61B 5/7217 |
| 2019/0381318 A1 | 12/2019 | Sinclair et al. |
| 2020/0001086 A1 | 1/2020 | Huertas Fernandez et al. |
| 2020/0001091 A1 | 1/2020 | Marnfeldt |
| 2020/0038660 A1* | 2/2020 | Torgerson .......... A61N 1/36164 |
| 2020/0138324 A1 | 5/2020 | Sinclair et al. |
| 2020/0147393 A1 | 5/2020 | Zhang et al. |
| 2020/0305744 A1 | 10/2020 | Weerakoon et al. |
| 2020/0305745 A1 | 10/2020 | Wagenbach et al. |
| 2020/0335221 A1 | 10/2020 | Fichtinger et al. |
| 2020/0391037 A1 | 12/2020 | Grado et al. |
| 2021/0016091 A1 | 1/2021 | Parker et al. |
| 2021/0046322 A1 | 2/2021 | Zhang et al. |
| 2021/0121696 A1* | 4/2021 | Parker .................. A61B 5/4035 |
| 2021/0236821 A1 | 8/2021 | Sinclair et al. |
| 2021/0267523 A1 | 9/2021 | Donoghue et al. |
| 2021/0339014 A1 | 11/2021 | Dinsmoor et al. |
| 2022/0040486 A1 | 2/2022 | Moffitt |
| 2022/0111213 A1 | 4/2022 | Cassar et al. |
| 2022/0151535 A1 | 5/2022 | Parker et al. |
| 2022/0218995 A1 | 7/2022 | Block et al. |
| 2022/0233866 A1 | 7/2022 | Gururaj et al. |
| 2022/0296892 A1 | 9/2022 | Esteller et al. |
| 2022/0296893 A1 | 9/2022 | Steinke et al. |
| 2022/0339448 A1 | 10/2022 | Jayakumar et al. |
| 2023/0023842 A1 | 1/2023 | Steinke et al. |
| 2023/0062062 A1 | 3/2023 | Litvak et al. |
| 2023/0069981 A1 | 3/2023 | Isaacson et al. |
| 2023/0099390 A1 | 3/2023 | Esteller et al. |
| 2023/0141183 A1 | 5/2023 | Moore et al. |
| 2023/0201597 A1 | 6/2023 | Haddock et al. |
| 2023/0271015 A1 | 8/2023 | Malekmohammadi et al. |

FOREIGN PATENT DOCUMENTS

| | | | |
|---|---|---|---|
| CN | 107280665 A | * 6/2017 | .......... A61B 5/7203 |
| CN | 107280665 A | * 10/2017 | |

(56) References Cited

FOREIGN PATENT DOCUMENTS

| | | |
|---|---|---|
| EP | 3229891 A1 | 10/2017 |
| WO | 2016/205231 A1 | 12/2016 |
| WO | 2018/008034 A2 | 1/2018 |
| WO | 2018/163178 A1 | 9/2018 |
| WO | 2018/213872 A1 | 11/2018 |
| WO | 2019/070406 A1 | 4/2019 |
| WO | 2019/210371 A1 | 11/2019 |
| WO | 2019/211314 A1 | 11/2019 |
| WO | 2019/217079 A1 | 11/2019 |
| WO | 2020/223165 A1 | 11/2020 |
| WO | 2021/026151 | 2/2021 |
| WO | 2021/080727 A1 | 4/2021 |

OTHER PUBLICATIONS

Gmel, Gerrit E., et al., "A New Biomarker for Closed-Loop Deep Brain Stimulation in the Subthalamic Nucleus for Patients with Parkinson's Disease," IEEE Biomedical Circuits and Systems Conference (BioCAS) Proceedings, Lausanne, 2014, pp. 500-503.

Gmel, Gerrit E., et al., "A New Biomarker for Subthalamic Deep Brain Stimulation for Patients with Advanced Parkinson's Disease—A Pilot Study," J. Neural Eng., 12, 2015, 11 pages.

Gmel, Gerrit Eduard, "Evoked Brain Neural Potentials," Dissertation for The University of New South Wales, Sep. 2016, 231 pages.

Kent, Alexander Rafael, et al., "Characterization of Evoked Potentials During Deep Brain Stimulation in the Thalamus," Dissertation Submitted in the Department of Biomedical Engineering Duke University, 2013, 320 pages.

Kent, Alexander R., et al., "Neural Origin of Evoked Potentials During Thalamic Deep Brain Stimulation," J Neurophysiol, 110, 2013, pp. 826-843.

Kent, A.R., et al., "Recording Evoked Potentials During Deep Brain Stimulaton: Development and Validation of Instrumentation to Suppress to Stimulus Artefact," J Neural Eng., 9(3), Jun. 2012, 30 pages.

Kirsch AD, et al., "Anodic Versus Cathodic Neurostimulation of the Subthalamic Nucleus: A Randomized-Controlled Study of Acute Clinical Effects," Parkinsonism and Related Disorders, 55, 2018, pp. 61-67.

Laarne, Paivi, et al., "Accuracy of Two Dipolar Inverse Algorithms Applying Reciprocity for Forward Calculation," Computers and Biomedical Research, vol. 33, Issue 3, pp. 172-185, Jun. 2000.

Moffitt, Michael A., et al., "Electrical Localization of Neural Activity in the Dorsal Horn of the Spinal Cord: A Modeling Study," Annals of Biomedical Engineering, 32(12), pp. 1694-1709, 2004.

Pascual-Marqui, RD, "Standardized Low-Resolution Brain Electromagnetic Tomography (sLORETA): Technical Details," Methods Find Exp Clin Pharmacol, 24 Suppl D, 5-12. 2002.

Sinclair, Nicholas C., et al., "Subthalamic Nucleus Deep Brain Stimulation Evokes Resonant Neural Activity," Annals of Neurology, 83(5), pp. 1027-1031, May 4, 2018.

Sinclair, Nicholas C., et al., "Subthalamic Nucleus Deep Brain Stimulation Evokes Resonant Neural Activity," Poster, 2019, 1 page.

Sinclair, Nicholas C., et al., "Deep Brain Stimulation for Parkinson's Disease Modulates High-Frequency Evoked and Spontaneous Neural Activity," Neurobiology of Disease, vol. 130, 104522, Oct. 2019.

Sinclair, Nicholas C., et al., "On the Neural Basis of Deep Brain Stimulation Evoked Resonant Activity," Biomed. Phys. Eng. Express, 5, 2019, 9 pages.

Sinclair, Nicholas C., et al., "Directional Deep Brain Stimulation Evoked Resonant Neural Activity (ERNA)," Poster, 2020, 1 page.

Thevathasan, Wesley, et al., "Tailoring Subthalamic Nucleus Deep Brain Stimulation for Parkinson's Disease Using Evoked Resonant Neural Activity," Frontiers in Human Neuroscience, vol. 14, Article 71, Feb. 2020, 6 pages.

Walker, Harrison, MD, et al., Directional Subthalamic Nucleus DBS for Parkinson's Disease: Year 3 Interim Analyses, UAB Medicine Poster, 2020, 1 page.

Wiest, C., et al., "Local Field Potential Activity Dynamics in Response to Deep Brain Stimulation of the Subthalamic Nucleus in Parkinson's Disease." Neurobiology of Disease, 2019, 41 pages.

Frankemolle, M. M., et al., "Reversing Cognitive-Motor Impairments in Parkinson's Disease Patients Using a Computational Modelling Approach to Deep Brain Stimulation Programming," Brain, 2010, pp. 1-16.

Georgopoulos, Apostolos P., et al., "On the Relations Between the Direction of Two-Dimensional Arm Movements and Cell Discharge in Primate Motor Cortex," The Journal of Neuroscience, vol. 2, No. 11, pp. 1527-1537, 1982.

Hatsopoulos, Nicholas G. et al., "Sensing with the Motor Cortex," J. Neuron, 72(3), 22 pages, 2011.

Shils, Jay, et al., "Motor Evoked Potential Recordings During Segmented DBS—A Feasibility Study," Oper Neurosurg (Hagerstown), Mar. 15, 2021, 20(4), pp. 419-425.

Wiest, C. et al., "Local Field Potential Activity Dynamics in Response to Deep Brain Stimulation of the Subthalamic Nucleus in Parkinson's Disease," Neurobiology of Disease, 143, 2020, 15 pages.

Wiest, C., et al, "Subthalamic Deep Brain Stimulation Induces Finely-Tuned Gamma Oscillations in the Absence of Levodopa," Neurobiology of Disease, 152, 105287, 2021, 13 pages.

Zelmann, Rina, et al., "Automatic Optimization of Depth Electrode Trajectory Planning," Montreal Neurological Institute Neurology and Neurosurgery, CLIP 2013, LNCS 8361, 2014, pp. 99-104.

Beriault, Silvain, et al., "A Multi-Modal Approach to Computer-Assisted Deep Brain Stimulation Trajectory Planning," International Journal of Computer Assisted Radiology and Surgery, 7, 2012, pp. 687-704.

Beriault, Silvain, et al., "A Prospective Evaluation of Computer-Assisted Deep Brain Stimulation Trajectory Planning," Montreal Neurological Institute McConnell Brain Imaging Centre, CLIP 2012, LNCS 7761, 2013, pp. 42-49.

\* cited by examiner

NEURAL FEEDBACK ASSISTED DBS

CROSS-REFERENCE TO RELATED APPLICATIONS

This application is a non-provisional application based on U.S. Provisional Patent Application Ser. No. 63/148,740, filed Feb. 12, 2021, which is incorporated herein by reference, and to which priority is claimed.

FIELD OF THE INVENTION

This application relates to deep brain stimulation (DBS), and more particularly, to methods and systems for using sensed neural responses for facilitating aspects of DBS.

INTRODUCTION

Implantable neurostimulator devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Deep Brain Stimulation (DBS). DBS has been applied therapeutically for the treatment of neurological disorders, including Parkinson's Disease, essential tremor, dystonia, and epilepsy, to name but a few. Further details discussing the treatment of diseases using DBS are disclosed in U.S. Pat. Nos. 6,845,267, 6,845,267, and 6,950,707. However, the present invention may find applicability with any implantable neurostimulator device system.

Each of these neurostimulation systems, whether implantable or external, typically includes one or more electrode carrying stimulation leads, which are implanted at the desired stimulation site, and a neurostimulator, used externally or implanted remotely from the stimulation site, but coupled either directly to the neurostimulation lead(s) or indirectly to the neurostimulation lead(s) via a lead extension. The neurostimulation system may further comprise a handheld external control device to remotely instruct the neurostimulator to generate electrical stimulation pulses in accordance with selected stimulation parameters. Typically, the stimulation parameters programmed into the neurostimulator can be adjusted by manipulating controls on the external control device to modify the electrical stimulation provided by the neurostimulator system to the patient.

Thus, in accordance with the stimulation parameters programmed by the external control device, electrical pulses can be delivered from the neurostimulator to the stimulation electrode(s) to stimulate or activate a volume of tissue in accordance with a set of stimulation parameters and provide the desired efficacious therapy to the patient. The best stimulus parameter set will typically be one that delivers stimulation energy to the volume of tissue that must be stimulated in order to provide the therapeutic benefit (e.g., treatment of movement disorders), while minimizing the volume of non-target tissue that is stimulated. A typical stimulation parameter set may include the electrodes that are acting as anodes or cathodes, as well as the amplitude, duration, and rate of the stimulation pulses.

Non-optimal electrode placement and stimulation parameter selections may result in excessive energy consumption due to stimulation that is set at too high an amplitude, too wide a pulse duration, or too fast a frequency; inadequate or marginalized treatment due to stimulation that is set at too low an amplitude, too narrow a pulse duration, or too slow a frequency; or stimulation of neighboring cell populations that may result in undesirable side effects. For example, bilateral DBS of the subthalamic nucleus has been shown to provide effective therapy for improving the major motor signs of advanced Parkinson's disease, and although the bilateral stimulation of the subthalamic nucleus is considered safe, an emerging concern is the potential negative consequences that it may have on cognitive functioning and overall quality of life (see A. M. M. Frankemolle, et al., Reversing Cognitive-Motor Impairments in Parkinson's Disease Patients Using a Computational Modelling Approach to Deep Brain Stimulation Programming, Brain 2010; pp. 1-16). In large part, this phenomenon is due to the small size of the subthalamic nucleus. Even with the electrodes are located predominately within the sensorimotor territory, the electrical field generated by DBS is non-discriminately applied to all neural elements surrounding the electrodes, thereby resulting in the spread of current to neural elements affecting cognition. As a result, diminished cognitive function during stimulation of the subthalamic nucleus may occur do to non-selective activation of non-motor pathways within or around the subthalamic nucleus.

The large number of electrodes available, combined with the ability to generate a variety of complex stimulation pulses, presents a huge selection of stimulation parameter sets to the clinician or patient. In the context of DBS, neurostimulation leads with a complex arrangement of electrodes that not only are distributed axially along the leads, but are also distributed circumferentially around the neurostimulation leads as segmented electrodes, can be used.

To facilitate such selection, the clinician generally programs the external control device, and if applicable the neurostimulator, through a computerized programming system. This programming system can be a self-contained hardware/software system, or can be defined predominantly by software running on a standard personal computer (PC) or mobile platform. The PC or custom hardware may actively control the characteristics of the electrical stimulation generated by the neurostimulator to allow the optimum stimulation parameters to be determined based on patient feedback and to subsequently program the external control device with the optimum stimulation parameters.

When electrical leads are implanted within the patient, the computerized programming system may be used to instruct the neurostimulator to apply electrical stimulation to test placement of the leads and/or electrodes, thereby assuring that the leads and/or electrodes are implanted in effective locations within the patient. The system may also instruct the user how to improve the positioning of the leads, or confirm when a lead is well-positioned. Once the leads are correctly positioned, a fitting procedure, which may be referred to as a navigation session, may be performed using the computerized programming system to program the external control device, and if applicable the neurostimulator, with a set of stimulation parameters that best addresses the neurological disorder(s).

In the context of DBS, the brain is dynamic (e.g., due to disease progression, motor re-learning, or other changes), and a program (i.e., a set of stimulation parameters) that is useful for a period of time may not maintain its effectiveness and/or the expectations of the patient may increase. Further, physicians typically treat the patient with stimulation and medication, and proper amounts of each are required for optimal therapy. In particular, a patient's stimulation needs may be impacted by their medication state. Additionally, the need for stimulation and/or medication may fluctuate across the day and week, depending on activities of daily living, especially sleep and activity.

Thus, there is a need for methods and systems that assist a clinician in obtaining an optimum lead placement during implantation process and to determine optimum stimulation parameters for treating the patient. There is also a need for closed loop feedback that can be used to adjust stimulation parameters as the patient's stimulation needs change with time or based on their medication state.

SUMMARY

Disclosed here is a medical device, comprising: an implantable pulse generator (IPG) configured for implantation in a patient and comprising a plurality of electrode nodes, each electrode node configured to be coupled to an electrode configured to contact a patient's neural tissue; and control circuitry configured to: control stimulation circuitry to issue stimulation at a first one or more of the plurality of electrode nodes, record an electrical signal at a second one or more of the plurality of electrode nodes, classify the recorded electrical signal according to one or more classification criteria to determine if the recorded electrical signal contains an evoked neural response of interest, if the recorded electrical signal does contain a neural response of interest, extract one or more features of the neural response of interest, and adjust stimulation based on the one or more features. If the signal does not contain a neural response of interest, then the signal may be rejected, that is, treated as not informative. According to some embodiments, determining if the recorded electrical signal contains a neural response of interest comprises determining if the electrical signal comprises one or more peaks or troughs with a prominence exceeding a predetermined threshold value or values. According to some embodiments, determining if the recorded electrical signal contains a neural response of interest comprises determining if the electrical signal comprises a number of peaks meeting or exceeding a predetermined threshold number of peaks within a predetermined time window. According to some embodiments, determining if the recorded electrical signal contains a neural response of interest comprises determining if the electrical signal comprises one or more peaks with amplitudes meeting or exceeding a predetermined amplitude threshold. According to some embodiments, determining if the recorded electrical signal contains a neural response of interest comprises determining if the electrical signal comprises one or more components within a range of predetermined frequencies and exceeding one or more predetermined thresholds. According to some embodiments, determining if the recorded electrical signal contains a neural response of interest comprises converting the recorded electrical signal from a time domain signal to a frequency domain signal. According to some embodiments, determining if the recorded electrical signal contains a neural response of interest further comprises determining if one or more relative band powers in one or more predetermined frequency ranges of the frequency domain signal meet or exceed one or more predetermined thresholds. According to some embodiments, determining if the recorded electrical signal contains a neural response of interest comprises assigning a confidence value that a neural response of interest is present and rejecting the recorded electrical signal unless the confidence value meets or exceeds a predetermined threshold. According to some embodiments, the neural response of interest is an oscillating neural response. According to some embodiments, the one or more features of the neural response of interest comprises one or more of a band power, a peak power, a full width at half max (FWHM), or a decay constant. According to some embodiments, the one or more features of the neural response of interest comprises one or more of a peak amplitude or a number of peaks. According to some embodiments, the recorded electrical signal is a time domain signal, and wherein the control circuitry is configured to determine a frequency domain signal corresponding to the time domain signal. According to some embodiments, the step of classifying the electrical signal is performed on the frequency domain signal. According to some embodiments, the step of extracting one or more features of the neural response of interest is performed on the frequency domain signal. According to some embodiments, the step of extracting one or more features of the neural response of interest is performed on the time domain signal. According to some embodiments, the control circuitry is further configured to record the one or more features of the neural response. According to some embodiments, the control circuitry is configured to classify the recorded signal if it does not contain a neural response of interest.

Also disclosed herein is a method for providing stimulation to a patient's neural tissue, wherein the patient is implanted with one or more electrode leads comprising a plurality of electrodes, the method comprising: issuing stimulation at a first one or more of the plurality of electrodes, recording an electrical signal at a second one or more of the plurality of electrodes, classifying the recorded electrical signal according to one or more classification criteria to determine if the recorded electrical signal contains an evoked neural response of interest, if the recorded electrical signal does contain a neural response of interest, extract one or more features of the neural response of interest, and adjusting stimulation based on the one or more features. According to some embodiments, determining if the recorded electrical signal contains a neural response of interest comprises determining if the electrical signal comprises one or more peaks or troughs with a prominence exceeding a predetermined threshold value or values. According to some embodiments, determining if the recorded electrical signal contains a neural response of interest comprises determining if the electrical signal comprises a number of peaks meeting or exceeding a predetermined threshold number of peaks within a predetermined time window. According to some embodiments, determining if the recorded electrical signal contains a neural response of interest comprises determining if the electrical signal comprises one or more peaks with amplitudes meeting or exceeding a predetermined amplitude threshold. According to some embodiments, determining if the recorded electrical signal contains a neural response of interest comprises determining if the electrical signal comprises one or more components within a range of predetermined frequencies and exceeding one or more predetermined thresholds. According to some embodiments, determining if the recorded electrical signal contains a neural response of interest comprises converting the recorded electrical signal from a time domain signal to a frequency domain signal. According to some embodiments, determining if the recorded electrical signal contains a neural response of interest further comprises determining if one or more relative band powers in one or more predetermined frequency ranges of the frequency domain signal meet or exceed one or more predetermined thresholds. According to some embodiments, determining if the recorded electrical signal contains a neural response of interest comprises assigning a confidence value that a neural response of interest is present and rejecting the recorded electrical signal unless the confidence value meets or exceeds a predetermined threshold. According to some embodiments, the neural response of interest is an oscillating neural response. According to some embodiments, the one or more features of the neural response of interest comprises one or more of a band power, a peak power, a full width at half max (FWHM), or a decay constant. According to some embodiments, the one or more features of the neural response of interest comprises one or more of a peak amplitude or a number of peaks. According to some embodiments, the recorded electrical signal is a time domain signal, and wherein the control circuitry is configured to determine a frequency domain signal corresponding to the time domain signal. According to some embodiments, the step of classifying the electrical signal is performed on the frequency domain signal. According to some embodiments, the step of extracting one or more features of the neural response of interest is performed on the frequency domain signal. According to some embodiments, the step of extracting one or more features of the neural response of interest is performed on the time domain signal. According to some embodiments, the method further comprises recording the one or more features of the neural response. According to some embodiments, the method further comprises classifying the recorded signal if it does not contain a neural response of interest. Also disclosed herein is a non-transitory computer-readable media comprising instructions, which, when executed by a processor of a machine, configure the machine to perform any of the methods described in this paragraph.

Also disclosed herein is a method of implanting a stimulation lead in the brain of a patient, wherein the stimulation lead comprises a plurality of electrodes, the method comprising: positioning the lead at a first position in the patient's brain, using the electrodes to apply stimulation at one or more stimulation locations upon the lead, recording electrical signals at one or more of the plurality of electrodes, classifying the recorded electrical signals according to one or more classification criteria to determine if the recorded electrical signals contain an evoked neural response of interest, if the recorded electrical signals contain a neural response of interest, extracting one or more features of the neural response of interest, and using the one or more features to determine one or more of (i) whether to move the lead to a new position or (ii) to adjust stimulation parameters based on the evoked responses. According to some embodiments, determining if the recorded electrical signal contains a neural response of interest comprises determining if the electrical signal comprises one or more peaks or troughs with a prominence exceeding a predetermined threshold value or values. According to some embodiments, determining if the recorded electrical signal contains a neural response of interest comprises determining if the electrical signal comprises a number of peaks meeting or exceeding a predetermined threshold number of peaks within a predetermined time window. According to some embodiments, determining if the recorded electrical signal contains a neural response of interest comprises determining if the electrical signal comprises one or more peaks with amplitudes meeting or exceeding a predetermined amplitude threshold. According to some embodiments, determining if the recorded electrical signal contains a neural response of interest comprises determining if the electrical signal comprises one or more components within a range of predetermined frequencies and exceeding one or more predetermined thresholds. According to some embodiments, determining if the recorded electrical signal contains a neural response of interest comprises converting the recorded electrical signal from a time domain signal to a frequency domain signal. According to some embodiments, determining if the recorded electrical signal contains a neural response of interest further comprises determining if one or more relative band powers in one or more predetermined frequency ranges of the frequency domain signal meet or exceed one or more predetermined thresholds. According to some embodiments, determining if the recorded electrical signal contains a neural response of interest comprises assigning a confidence value that a neural response of interest is present and rejecting the recorded electrical signal unless the confidence value meets or exceeds a predetermined threshold. According to some embodiments, the neural response of interest is an oscillating neural response. According to some embodiments, the one or more features of the neural response of interest comprises one or more of a band power, a peak power, a full width at half max (FWHM), or a decay constant. According to some embodiments, the one or more features of the neural response of interest comprises one or more of a peak amplitude or a number of peaks. According to some embodiments, the recorded electrical signal is a time domain signal, and wherein the control circuitry is configured to determine a frequency domain signal corresponding to the time domain signal. According to some embodiments, the step of classifying the electrical signal is performed on the frequency domain signal. According to some embodiments, the step of extracting one or more features of the neural response of interest is performed on the frequency domain signal. According to some embodiments, the step of extracting one or more features of the neural response of interest is performed on the time domain signal. According to some embodiments, the method further comprises adjusting the stimulation based on the one or more features of the neural response. According to some embodiments, the method further comprises storing the one or more features of the neural response. According to some embodiments, the method further comprises displaying the one or more features on a graphical user interface. According to some embodiments, the method further comprises rejecting the recorded signal if it does not contain a neural response of interest. Also disclosed herein is a non-transitory computer-readable media comprising instructions, which, when executed by a processor of a machine, configure the machine to perform any of the methods described in this paragraph.

Also disclosed herein is a system for facilitating the implantation of an electrode lead in the brain of a patient, wherein the electrode lead comprises a plurality of electrodes, the system comprising: control circuitry configured to: receive an indication that the lead is positioned at a first position in the patient's brain, use one or more of the electrodes to apply stimulation at one or more stimulation locations upon the lead, record electrical signals at one or more of the plurality of electrodes, classify the recorded electrical signals according to one or more classification criteria to determine if the recorded electrical signals contain an evoked neural response of interest, if the recorded electrical signals contain a neural response of interest, extract one or more features of the neural response of interest, and use the one or more features to determine one or more of (i) whether to move the lead to a new position or (ii) to adjust stimulation parameters based on the evoked responses. According to some embodiments, determining if the recorded electrical signal contains a neural response of interest comprises determining if the electrical signal comprises one or more peaks or troughs with a prominence exceeding a predetermined threshold value or values. According to some embodiments, determining if the recorded electrical signal contains a neural response of interest comprises determining if the electrical signal comprises a number of peaks meeting or exceeding a predetermined threshold number of peaks within a predetermined time window. According to some embodiments, determining if the recorded electrical signal contains a neural response of interest comprises determining if the electrical signal comprises one or more peaks with amplitudes meeting or exceeding a predetermined amplitude threshold. According to some embodiments, determining if the recorded electrical signal contains a neural response of interest comprises determining if the electrical signal comprises one or more components within a range of predetermined frequencies and exceeding one or more predetermined thresholds. According to some embodiments, determining if the recorded electrical signal contains a neural response of interest comprises converting the recorded electrical signal from a time domain signal to a frequency domain signal. According to some embodiments, determining if the recorded electrical signal contains a neural response of interest further comprises determining if one or more relative band powers in one or more predetermined frequency ranges of the frequency domain signal meet or exceed one or more predetermined thresholds. According to some embodiments, determining if the recorded electrical signal contains a neural response of interest comprises assigning a confidence value that a neural response of interest is present and rejecting the recorded electrical signal unless the confidence value meets or exceeds a predetermined threshold. According to some embodiments, the neural response of interest is an oscillating neural response. According to some embodiments, the one or more features of the neural response of interest comprises one or more of a band power, a peak power, a full width at half max (FWHM), or a decay constant. According to some embodiments, the one or more features of the neural response of interest comprises one or more of a peak amplitude or a number of peaks. According to some embodiments, the recorded electrical signal is a time domain signal, and wherein the control circuitry is configured to determine a frequency domain signal corresponding to the time domain signal. According to some embodiments, the step of classifying the electrical signal is performed on the frequency domain signal. According to some embodiments, the step of extracting one or more features of the neural response of interest is performed on the frequency domain signal. According to some embodiments, the step of extracting one or more features of the neural response of interest is performed on the time domain signal. According to some embodiments, the control circuitry if further configured to adjust the stimulation based on the one or more features of the neural response. According to some embodiments, the control circuitry is further configured to store the one or more features of the neural response. According to some embodiments, the control circuitry is further configured to cause the one or more features of the neural response to be displayed on a graphical user interface. According to some embodiments, the control circuitry is configured to reject the recorded signal if it does not contain a neural response of interest.

Also disclosed herein is a method of determining a stimulation configuration for a patient implanted with one or more electrode leads in the patient's brain, each electrode lead comprising a plurality of electrodes, the method comprising: (i) providing stimulation using one or more of the electrodes as stimulating electrodes, (ii) recording electrical signals at a plurality of electrodes as recording electrodes, (iii) classifying each of the recorded electrical signals according to one or more classification criteria to determine if each of the recorded electrical signals contain a neural response of interest, (iv) for each electrical signal containing a neural response of interest, extracting one or more features of the neural response, (v) iteratively repeating steps (i)-(iv) with a different one or more electrodes as the stimulating electrodes with each iteration, and (vi) using the extracted features to determine a preferred stimulation configuration. According to some embodiments, determining the stimulation configuration comprises determining a plurality of electrodes to use for a multi-site stimulation paradigm. According to some embodiments, the multi-site stimulation paradigm comprises coordinated reset stimulation. According to some embodiments, determining the stimulation configuration comprises determining a neural coupling between two or more of the electrodes and selecting the two or more of the electrodes to provide therapeutic stimulation based on the neural coupling. According to some embodiments, determining the neural coupling comprises using graph theory analysis (GTA). According to some embodiments, the GTA comprises modeling each of the plurality electrodes as vertices of a graph and modeling the extracted one or more features of the neural response as edges of the graph. According to some embodiments, the method further comprises determining therapeutic stimulation parameters based on weights of the edges. According to some embodiments, determining the stimulation configuration comprises modeling the extracted neural features in three-dimensions wherein a first dimension represents time, a second dimension represents the stimulating electrodes, and a third dimension represents the recording electrodes. According to some embodiments, the method further comprises using independent components analysis to determine dominant components of the modeled extracted neural features and determining the stimulation configuration based on the dominant components. According to some embodiments, determining if the recorded electrical signal contains a neural response of interest comprises determining if the electrical signal comprises peaks with a prominence exceeding a predetermined threshold value. According to some embodiments, determining if the recorded electrical signal contains a neural response of interest comprises determining if the electrical signal comprises a number of peaks meeting or exceeding a predetermined threshold number of peaks within a predetermined time window. According to some embodiments, determining if the recorded electrical signal contains a neural response of interest comprises determining if the electrical signal comprises determining if the electrical signal comprises one or more peaks with amplitudes meeting or exceeding a predetermined amplitude threshold. According to some embodiments, determining if the recorded electrical signal contains a neural response of interest comprises determining if the electrical signal comprises one or more components within a range of predetermined frequencies and exceeding a predetermined threshold. According to some embodiments, determining if the recorded electrical signal contains a neural response of interest comprises converting the recorded electrical signal from a time domain signal to a frequency domain signal.

According to some embodiments, determining if the recorded electrical signal contains a neural response of interest further comprises determining if a relative band power in a predetermined frequency range of the frequency domain signal meets or exceeds a predetermined threshold. According to some embodiments, determining if the recorded electrical signal contains a neural response of interest comprises determining a confidence value that a neural response of interest is present and rejecting the recorded electrical signal unless the confidence value meets or exceeds a predetermined threshold. According to some embodiments, the neural response of interest is an oscillating neural response. According to some embodiments, the one or more features of the neural response of interest comprises one or more of a band power, a peak power, a full width at half max (FWHM), or a decay constant. According to some embodiments, the one or more features of the neural response of interest comprises one or more of a peak amplitude or a number of peaks. According to some embodiments, the recorded electrical signal is a time domain signal, and the method further comprises determining a frequency domain signal corresponding to the time domain signal. According to some embodiments, the step of classifying the electrical signal is performed on the frequency domain signal. According to some embodiments, the step of extracting one or more features of the neural response of interest is performed on the frequency domain signal. According to some embodiments, the step of extracting one or more features of the neural response of interest is performed on the time domain signal. Also disclosed herein is a non-transitory computer-readable media comprising instructions, which, when executed by a processor of a machine, configure the machine to perform any of the methods described in this paragraph.

Also disclosed herein is a device for determining a stimulation configuration for a patient implanted with one or more electrode leads in the patient's brain, each electrode lead comprising a plurality of electrodes, the device comprising: control circuitry configured to: (i) cause stimulation circuitry to provide stimulation using one or more of the electrodes as stimulating electrodes, (ii) cause sensing circuitry to recording electrical signals at a plurality of electrodes as recording electrodes, (iii) classify each of the recorded electrical signals according to one or more classification criteria to determine if each of the recorded electrical signals contain a neural response of interest, (iv) for each electrical signal containing a neural response of interest, extract one or more features of the neural response, (v) iteratively repeat steps (i)-(iv) with a different one or more electrodes as the stimulating electrodes with each iteration, and (vi) use the extracted features to determine a preferred stimulation configuration. According to some embodiments, determining the stimulation configuration comprises determining a plurality of electrodes to use for a multi-site stimulation paradigm. According to some embodiments, the multi-site stimulation paradigm comprises coordinated reset stimulation. According to some embodiments, determining the stimulation configuration comprises determining a neural coupling between two or more of the electrodes and selecting the two or more of the electrodes to provide therapeutic stimulation based on the neural coupling. According to some embodiments, determining the neural coupling comprises using graph theory analysis (GTA). According to some embodiments, the GTA comprises modeling each of the plurality electrodes as vertices of a graph and modeling the extracted one or more features of the neural response as edges of the graph. According to some embodiments, the control circuitry is configured to determine therapeutic stimulation parameters based on weights of the edges. According to some embodiments, determining the stimulation configuration comprises modeling the extracted neural features in three-dimensions wherein a first dimension represents time, a second dimension represents the stimulating electrodes, and a third dimension represents the recording electrodes. According to some embodiments, the control circuitry is further configured to use independent components analysis to determine dominant components of the modeled extracted neural features and determining the stimulation configuration based on the dominant components. According to some embodiments, determining if the recorded electrical signal contains a neural response of interest comprises determining if the electrical signal comprises peaks with a prominence exceeding a predetermined threshold value. According to some embodiments, determining if the recorded electrical signal contains a neural response of interest comprises determining if the electrical signal comprises a number of peaks meeting or exceeding a predetermined threshold number of peaks within a predetermined time window. According to some embodiments, determining if the recorded electrical signal contains a neural response of interest comprises determining if the electrical signal comprises determining if the electrical signal comprises one or more peaks with amplitudes meeting or exceeding a predetermined amplitude threshold. According to some embodiments, determining if the recorded electrical signal contains a neural response of interest comprises determining if the electrical signal comprises one or more components within a range of predetermined frequencies and exceeding a predetermined threshold. According to some embodiments, determining if the recorded electrical signal contains a neural response of interest comprises converting the recorded electrical signal from a time domain signal to a frequency domain signal. According to some embodiments, determining if the recorded electrical signal contains a neural response of interest further comprises determining if a relative band power in a predetermined frequency range of the frequency domain signal meets or exceeds a predetermined threshold. According to some embodiments, determining if the recorded electrical signal contains a neural response of interest comprises determining a confidence value that a neural response of interest is present and rejecting the recorded electrical signal unless the confidence value meets or exceeds a predetermined threshold. According to some embodiments, the neural response of interest is an oscillating neural response. According to some embodiments, the one or more features of the neural response of interest comprises one or more of a band power, a peak power, a full width at half max (FWHM), or a decay constant. According to some embodiments, the one or more features of the neural response of interest comprises one or more of a peak amplitude or a number of peaks. According to some embodiments, the recorded electrical signal is a time domain signal, and wherein the control circuitry is configured to determine a frequency domain signal corresponding to the time domain signal. According to some embodiments, the step of classifying the electrical signal is performed on the frequency domain signal. According to some embodiments, the step of extracting one or more features of the neural response of interest is performed on the frequency domain signal. According to some embodiments, the step of extracting one or more features of the neural response of interest is performed on the time domain signal.

The invention may also reside in the form of a programmed external device (via its control circuitry) for carrying out the above methods, a programmed IPG or ETS (via its control circuitry) for carrying out the above methods, a system including a programmed external device and IPG or ETS for carrying out the above methods, or as a computer readable media for carrying out the above methods stored in an external device or IPG or ETS. The invention may also reside in one or more non-transitory computer-readable media comprising instructions, which when executed by a processor of a machine configure the machine to perform any of the above methods.

DETAILED DESCRIPTION

Figure 1A:
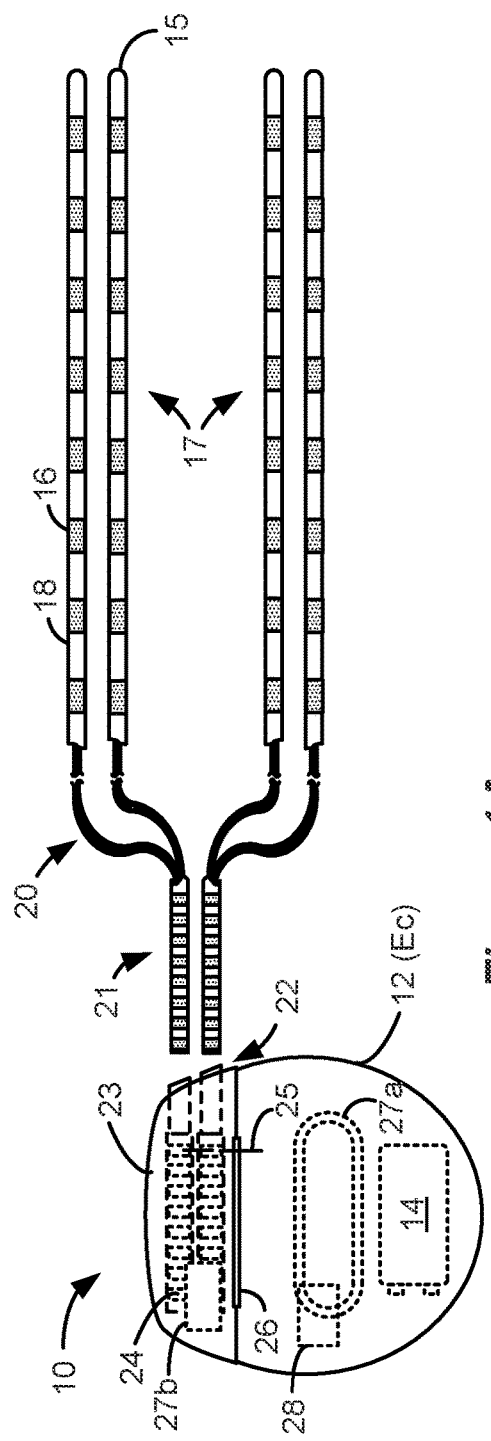
FIG. 1A shows an Implantable Pulse Generator (IPG).

A DBS or SCS system typically includes an Implantable Pulse Generator (IPG) 10 shown in FIG. 1A. The IPG 10 includes a biocompatible device case 12 that holds the circuitry and a battery 14 for providing power for the IPG to function. The IPG 10 is coupled to tissue-stimulating electrodes 16 via one or more electrode leads that form an electrode array 17. For example, one or more electrode leads 15 can be used having ring-shaped electrodes 16 carried on a flexible body 18.

Figure 1B:
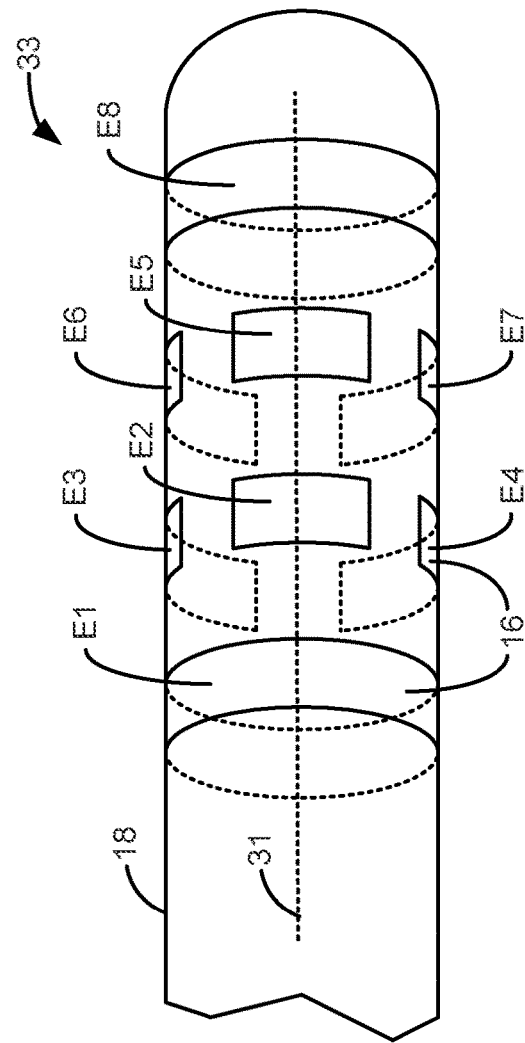
FIG. 1B shows a percutaneous lead having split-ring electrodes.

In yet another example shown in FIG. 1B, an electrode lead 33 can include one or more split-ring electrodes. In this example, eight electrodes 16 (E1-E8) are shown. Electrode E8 at the distal end of the lead and electrode E1 at a proximal end of the lead comprise ring electrodes spanning 360 degrees around a central axis of the lead 33. Electrodes E2, E3, and E4 comprise split-ring electrodes, each of which are located at the same longitudinal position along the central axis 31, but with each spanning less than 360 degrees around the axis. For example, each of electrodes E2, E3, and E4 may span 90 degrees around the axis 31, with each being separated from the others by gaps of 30 degrees. Electrodes E5, E6, and E7 also comprise split-ring electrodes, but are located at a different longitudinal position along the central axis 31 than are split ring electrodes E1, E2, and E3. As shown, the split-ring electrodes E1-E3 and E5-E7 may be located at longitudinal positions along the axis 31 between ring electrodes E1 and E8. However, this is just one example of a lead 33 having split-ring electrodes. In other designs, all electrodes can be split-ring, or there could be different numbers of split-ring electrodes at each longitudinal position (i.e., more or less than three), or the ring and split-ring electrodes could occur at different or random longitudinal positions, etc.

Lead wires 20 within the leads are coupled to the electrodes 16 and to proximal contacts 21 insertable into lead connectors 22 fixed in a header 23 on the IPG 10, which header can comprise an epoxy for example. Once inserted, the proximal contacts 21 connect to header contacts 24 within the lead connectors 22, which are in turn coupled by feedthrough pins 25 through a case feedthrough 26 to stimulation circuitry 28 within the case 12, which stimulation circuitry 28 is described below.

In the IPG 10 illustrated in FIG. 1A, there are thirty-two electrodes (E1-E32), split between four percutaneous leads 15, or contained on a single paddle lead 19, and thus the header 23 may include a 2×2 array of eight-electrode lead connectors 22. However, the type and number of leads, and the number of electrodes, in an IPG is application specific and therefore can vary. The conductive case 12 can also comprise an electrode (Ec).

In a DBS application, as is useful in the treatment of tremor in Parkinson's disease for example, the IPG 10 is typically implanted under the patient's clavicle (collarbone). Lead wires 20 are tunneled through the neck and the scalp and the electrode leads 15 (or 33) are implanted through holes drilled in the skull and positioned for example in the subthalamic nucleus (STN) and the pedunculopontine nucleus (PPN) in each brain hemisphere.

IPG 10 can include an antenna 27a allowing it to communicate bi-directionally with a number of external devices discussed subsequently. Antenna 27a as shown comprises a conductive coil within the case 12, although the coil antenna 27a can also appear in the header 23. When antenna 27a is configured as a coil, communication with external devices preferably occurs using near-field magnetic induction. IPG 10 may also include a Radio-Frequency (RF) antenna 27b. In FIG. 1A, RF antenna 27b is shown within the header 23, but it may also be within the case 12. RF antenna 27b may comprise a patch, slot, or wire, and may operate as a monopole or dipole. RF antenna 27b preferably communicates using far-field electromagnetic waves, and may operate in accordance with any number of known RF communication standards, such as Bluetooth, Bluetooth Low Energy (BLE), as described in U.S. Patent Publication 2019/0209851, Zigbee, WiFi, MICS, and the like.

Figure 2A:
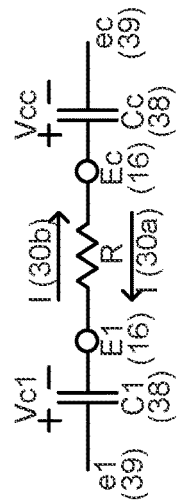
FIGS. 2A and 2B show an example of stimulation pulses (waveforms) producible by the IPG or by an External Trial Stimulator (ETS).

Stimulation in IPG 10 is typically provided by pulses each of which may include a number of phases such as 30a and 30b, as shown in the example of FIG. 2A. In the example shown, such stimulation is monopolar, meaning that a current is provided between at least one selected lead-based electrode (e.g., E1) and the case electrode Ec 12. Stimulation parameters typically include amplitude (current I, although a voltage amplitude V can also be used); frequency (f); pulse width (PW) of the pulses or of its individual phases such as 30a and 30b; the electrodes 16 selected to provide the stimulation; and the polarity of such selected electrodes, i.e., whether they act as anodes that source current to the tissue or cathodes that sink current from the tissue. These and possibly other stimulation parameters taken together comprise a stimulation program that the stimulation circuitry 28 in the IPG 10 can execute to provide therapeutic stimulation to a patient.

In the example of FIG. 2A, electrode E1 has been selected as a cathode (during its first phase 30a), and thus provides pulses which sink a negative current of amplitude −I from the tissue. The case electrode Ec has been selected as an anode (again during first phase 30a), and thus provides pulses which source a corresponding positive current of amplitude +I to the tissue. Note that at any time the current sunk from the tissue (e.g., −I at E1 during phase 30a) equals the current sourced to the tissue (e.g., +I at Ec during phase 30a) to ensure that the net current injected into the tissue is zero. The polarity of the currents at these electrodes can be changed: Ec can be selected as a cathode, and E1 can be selected as an anode, etc.

Figure 3:
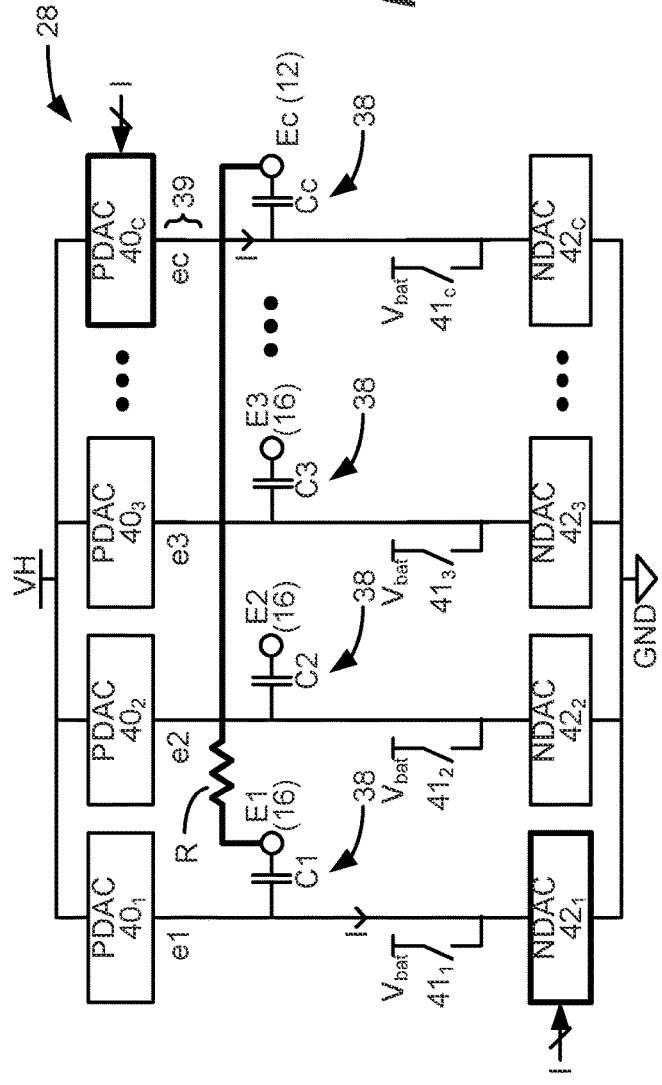
FIG. 3 shows an example of stimulation circuitry useable in the IPG or ETS.

IPG 10 as mentioned includes stimulation circuitry 28 to form prescribed stimulation at a patient's tissue. FIG. 3 shows an example of stimulation circuitry 28, which includes one or more current sources $40_i$ and one or more current sinks $42_i$. The sources and sinks $40_i$ and $42_i$ can comprise Digital-to-Analog converters (DACs), and may be referred to as PDACs $40_i$ and NDACs $42_i$ in accordance with the Positive (sourced, anodic) and Negative (sunk, cathodic) currents they respectively issue. In the example shown, a NDAC/PDAC $40_i/42_i$ pair is dedicated (hardwired) to a particular electrode node Ei 39. Each electrode node Ei 39 is connected to an electrode Ei 16 via a DC-blocking capacitor Ci 38, for the reasons explained below. PDACs $40_i$ and NDACs $42_i$ can also comprise voltage sources.

Proper control of the PDACs $40_i$ and NDACs $42_i$ allows any of the electrodes 16 and the case electrode Ec 12 to act as anodes or cathodes to create a current through a patient's tissue, R, hopefully with good therapeutic effect. In the example shown, and consistent with the first pulse phase 30a of FIG. 2A, electrode E1 has been selected as a cathode electrode to sink current from the tissue R and case electrode Ec has been selected as an anode electrode to source current to the tissue R. Thus PDAC $40_C$ and NDAC $42_1$ are activated and digitally programmed to produce the desired current, I, with the correct timing (e.g., in accordance with the prescribed frequency F and pulse width PW). Power for the stimulation circuitry 28 is provided by a compliance voltage VH, as described in further detail in U.S. Patent Application Publication 2013/0289665.

Other stimulation circuitries 28 can also be used in the IPG 10. In an example not shown, a switching matrix can intervene between the one or more PDACs $40_i$ and the electrode nodes ei 39, and between the one or more NDACs $42_i$ and the electrode nodes. Switching matrices allows one or more of the PDACs or one or more of the NDACs to be connected to one or more electrode nodes at a given time. Various examples of stimulation circuitries can be found in U.S. Pat. Nos. 6,181,969, 8,606,362, 8,620,436, U.S. Patent Application Publications 2018/0071520 and 2019/0083796. The stimulation circuitries described herein provide multiple independent current control (MICC) (or multiple independent voltage control) to guide the estimate of current fractionalization among multiple electrodes and estimate a total amplitude that provide a desired strength. In other words, the total anodic (or cathodic) current can be split among two or more electrodes and/or the total cathodic current can be split among two or more electrodes, allowing the stimulation location and resulting field shapes to be adjusted. For example, a "virtual electrode" may be created at a position between two physical electrodes by fractionating current between the two electrodes.

Much of the stimulation circuitry 28 of FIG. 3, including the PDACs $40_i$ and NDACs $42_i$, the switch matrices (if present), and the electrode nodes ei 39 can be integrated on one or more Application Specific Integrated Circuits (ASICs), as described in U.S. Patent Application Publications 2012/0095529, 2012/0092031, and 2012/0095519. As explained in these references, ASIC(s) may also contain other circuitry useful in the IPG 10, such as telemetry circuitry (for interfacing off chip with telemetry antennas 27a and/or 27b), circuitry for generating the compliance voltage VH, various measurement circuits, etc.

Also shown in FIG. 3 are DC-blocking capacitors Ci 38 placed in series in the electrode current paths between each of the electrode nodes ei 39 and the electrodes Ei 16 (including the case electrode Ec 12). The DC-blocking capacitors 38 act as a safety measure to prevent DC current injection into the patient, as could occur for example if there is a circuit fault in the stimulation circuitry 28. The DC-blocking capacitors 38 are typically provided off-chip (off of the ASIC(s)), and instead may be provided in or on a circuit board in the IPG 10 used to integrate its various components, as explained in U.S. Patent Application Publication 2015/0157861.

Figure 2B:
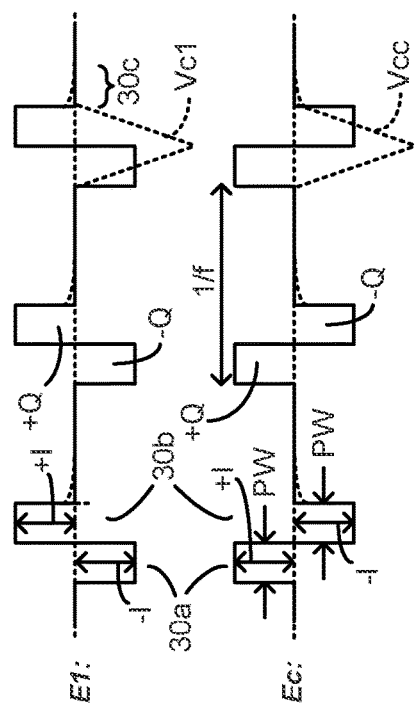

Referring again to FIG. 2A, the stimulation pulses as shown are biphasic, with each pulse comprising a first phase 30a followed thereafter by a second phase 30b of opposite polarity. Biphasic pulses are useful to actively recover any charge that might be stored on capacitive elements in the electrode current paths, such as on the DC-blocking capacitors 38. Charge recovery is shown with reference to both FIGS. 2A and 2B. During the first pulse phase 30a, charge will build up across the DC-blockings capacitors C1 and Cc associated with the electrodes E1 and Ec used to produce the current, giving rise to voltages Vc1 and Vcc which decrease in accordance with the amplitude of the current and the capacitance of the capacitors 38 (dV/dt=I/C). During the second pulse phase 30b, when the polarity of the current I is reversed at the selected electrodes E1 and Ec, the stored charge on capacitors C1 and Cc is actively recovered, and thus voltages Vc1 and Vcc increase and return to 0V at the end the second pulse phase 30b.

To recover all charge by the end of the second pulse phase 30b of each pulse (Vc1=Vcc=0V), the first and second phases 30a and 30b are charged balanced at each electrode, with the first pulse phase 30a providing a charge of −Q (−I*PW) and the second pulse phase 30b providing a charge of +Q (+I*PW) at electrode E1, and with the first pulse phase 30a providing a charge of +Q and the second pulse phase 30b providing a charge of −Q at the case electrode Ec. In the example shown, such charge balancing is achieved by using the same pulse width (PW) and the same amplitude (|I|) for each of the opposite-polarity pulse phases 30a and 30b. However, the pulse phases 30a and 30b may also be charged balance at each electrode if the product of the amplitude and pulse widths of the two phases 30a and 30b are equal, or if the area under each of the phases is equal, as is known.

FIG. 3 shows that stimulation circuitry 28 can include passive recovery switches $41_i$, which are described further in U.S. Patent Application Publications 2018/0071527 and 2018/0140831. Passive recovery switches $41_i$ may be attached to each of the electrode nodes ei 39, and are used to passively recover any charge remaining on the DC-blocking capacitors Ci 38 after issuance of the second pulse phase 30b—i.e., to recover charge without actively driving a current using the DAC circuitry. Passive charge recovery can be prudent, because non-idealities in the stimulation circuitry 28 may lead to pulse phases 30a and 30b that are not perfectly charge balanced.

Therefore, and as shown in FIG. 2A, passive charge recovery typically occurs after the issuance of second pulse phases 30b, for example during at least a portion 30c of the quiet periods between the pulses, by closing passive recovery switches $41_i$. As shown in FIG. 3, the other end of the switches $41_i$ not coupled to the electrode nodes ei 39 are connected to a common reference voltage, which in this example comprises the voltage of the battery 14, Vbat, although another reference voltage could be used. As explained in the above-cited references, passive charge recovery tends to equilibrate the charge on the DC-blocking capacitors 38 by placing the capacitors in parallel between the reference voltage (Vbat) and the patient's tissue. Note that passive charge recovery is illustrated as small exponentially decaying curves during 30c in FIG. 2A, which may be positive or negative depending on whether pulse phase 30a or 30b have a predominance of charge at a given electrode.

Passive charge recovery 30c may alleviate the need to use biphasic pulses for charge recovery, especially in the DBS context when the amplitudes of currents may be lower, and therefore charge recovery less of a concern. For example, and although not shown in FIG. 2A, the pulses provided to the tissue may be monophasic, comprising only a first pulse phase 30a. This may be followed thereafter by passive charge recovery 30c to eliminate any charge build up that occurred during the singular pulses 30a.

Figure 4:
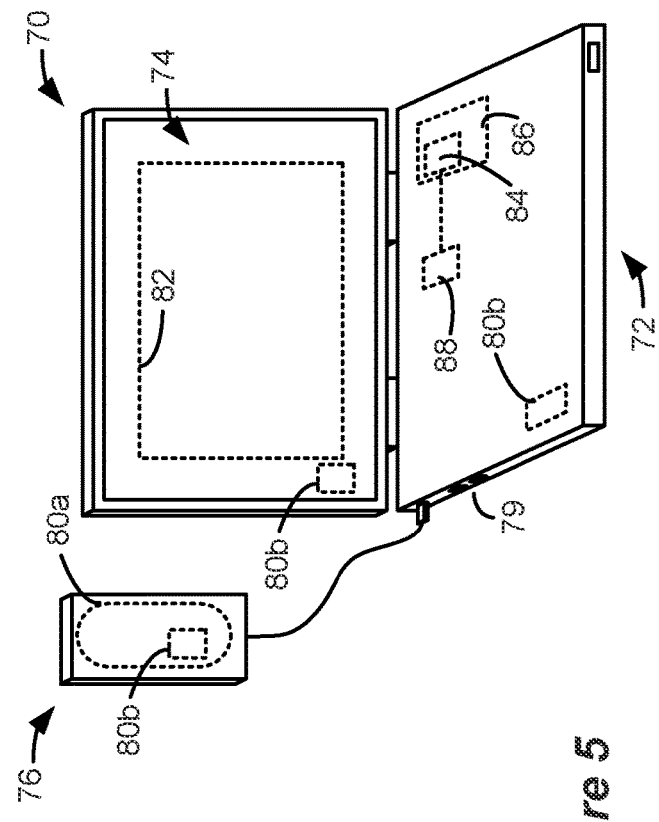
FIG. 4 shows an ETS environment useable to provide stimulation before implantation of an IPG.

FIG. 4 shows an external trial stimulation environment that may precede implantation of an IPG 10 in a patient, for example, during the operating room to test stimulation and confirm the lead position. During external trial stimulation, stimulation can be tried on the implant patient to evaluate side-effect thresholds and confirm that the lead is not too close to structures that cause side effects. Like the IPG 10, the ETS 50 can include one or more antennas to enable bi-directional communications with external devices such as those shown in FIG. 5. Such antennas can include a near-field magnetic-induction coil antenna 56a, and/or a far-field RF antenna 56b, as described earlier. ETS 50 may also include stimulation circuitry able to form stimulation in accordance with a stimulation program, which circuitry may be similar to or comprise the same stimulation circuitry 28 (FIG. 3) present in the IPG 10. ETS 50 may also include a battery (not shown) for operational power. The sensing capabilities described herein with regard to the IPG 10, may also be included in the ETS 50 for the purposes described below. As the IPG may include a case electrode, an ETS may provide one or more connections to establish similar returns; for example, using patch electrodes. Likewise, the ETS may communicate with the CP so that the CP can process the data as described below.

Figure 5:
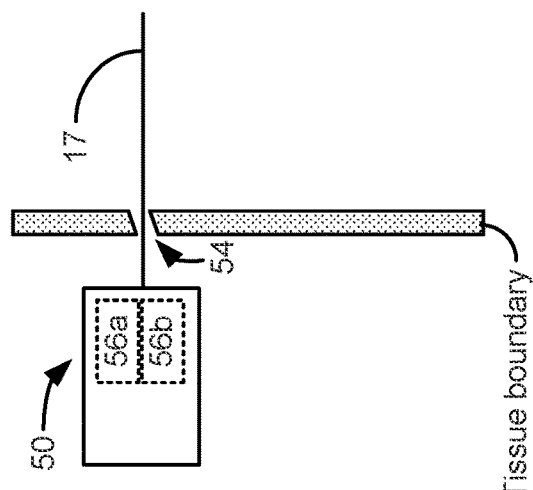
FIG. 5 shows various external devices capable of communicating with and programming stimulation in an IPG or ETS.
Figure 5:
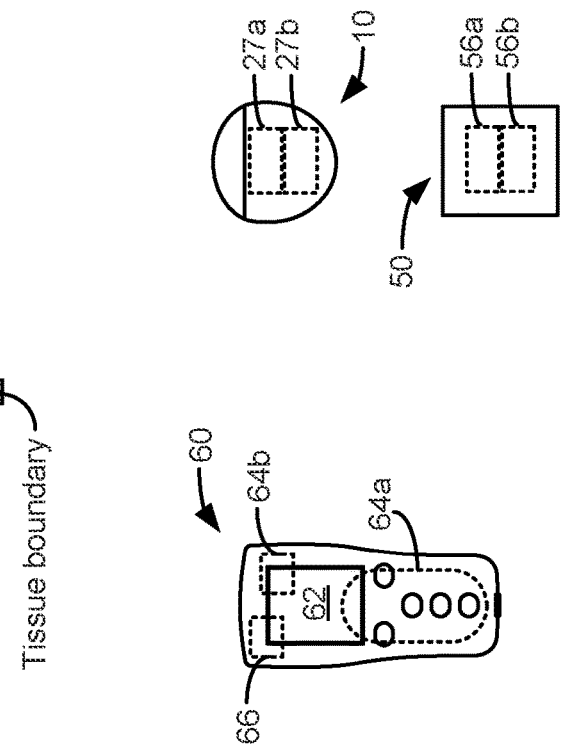

FIG. 5 shows various external devices that can wirelessly communicate data with the IPG 10 or ETS 50, including a patient hand-held external controller 60, and a clinician programmer (CP) 70. Both of devices 60 and 70 can be used to wirelessly transmit a stimulation program to the IPG 10 or ETS 50—that is, to program their stimulation circuitries to produce stimulation with a desired amplitude and timing described earlier. Both devices 60 and 70 may also be used to adjust one or more stimulation parameters of a stimulation program that the IPG 10 is currently executing. Devices 60 and 70 may also wirelessly receive information from the IPG 10 or ETS 50, such as various status information, etc.

External controller 60 can be as described in U.S. Patent Application Publication 2015/0080982 for example and may comprise a controller dedicated to work with the IPG 10 or ETS 50. External controller 60 may also comprise a general-purpose mobile electronics device such as a mobile phone which has been programmed with a Medical Device Application (MDA) allowing it to work as a wireless controller for the IPG 10 or ETS, as described in U.S. Patent Application Publication 2015/0231402. External controller 60 includes a user interface, preferably including means for entering commands (e.g., buttons or selectable graphical elements) and a display 62. The external controller 60's user interface enables a patient to adjust stimulation parameters, although it may have limited functionality when compared to the more-powerful clinician programmer 70, described shortly.

The external controller 60 can have one or more antennas capable of communicating with the IPG 10. For example, the external controller 60 can have a near-field magnetic-induction coil antenna 64a capable of wirelessly communicating with the coil antenna 27a or 56a in the IPG 10 or ETS 50. The external controller 60 can also have a far-field RF antenna 64b capable of wirelessly communicating with the RF antenna 27b or 56b in the IPG 10 or ETS 50.

Clinician programmer 70 is described further in U.S. Patent Application Publication 2015/0360038, and can comprise a computing device 72, such as a desktop, laptop, or notebook computer, a tablet, a mobile smart phone, a Personal Data Assistant (PDA)-type mobile computing device, etc. In FIG. 5, computing device 72 is shown as a laptop computer that includes typical computer user interface means such as a screen 74, a mouse, a keyboard, speakers, a stylus, a printer, etc., not all of which are shown for convenience. Also shown in FIG. 5 are accessory devices for the clinician programmer 70 that are usually specific to its operation as a stimulation controller, such as a communication "wand" 76 coupleable to suitable ports on the computing device 72, such as USB ports 79 for example.

The antenna used in the clinician programmer 70 to communicate with the IPG 10 or ETS 50 can depend on the type of antennas included in those devices. If the patient's IPG 10 or ETS 50 includes a coil antenna 27a or 56a, wand 76 can likewise include a coil antenna 80a to establish near-field magnetic-induction communications at small distances. In this instance, the wand 76 may be affixed in close proximity to the patient, such as by placing the wand 76 in a belt or holster wearable by the patient and proximate to the patient's IPG 10 or ETS 50. If the IPG 10 or ETS 50 includes an RF antenna 27b or 56b, the wand 76, the computing device 72, or both, can likewise include an RF antenna 80b to establish communication at larger distances. The clinician programmer 70 can also communicate with other devices and networks, such as the Internet, either wirelessly or via a wired link provided at an Ethernet or network port.

To program stimulation programs or parameters for the IPG 10 or ETS 50, the clinician interfaces with a clinician programmer graphical user interface (GUI) 82 provided on the display 74 of the computing device 72. As one skilled in the art understands, the GUI 82 can be rendered by execution of clinician programmer software 84 stored in the computing device 72, which software may be stored in the device's non-volatile memory 86. Execution of the clinician programmer software 84 in the computing device 72 can be facilitated by control circuitry 88 such as one or more microprocessors, microcomputers, FPGAs, DSPs, other digital logic structures, etc., which are capable of executing programs in a computing device, and which may comprise their own memories. For example, control circuitry 88 can comprise an i5 processor manufactured by Intel Corp, as described at https://www.intel.com/content/www/us/en/products/processors/core/i5-processors.html. Such control circuitry 88, in addition to executing the clinician programmer software 84 and rendering the GUI 82, can also enable communications via antennas 80a or 80b to communicate stimulation parameters chosen through the GUI 82 to the patient's IPG 10.

The user interface of the external controller 60 may provide similar functionality because the external controller 60 can include similar hardware and software programming as the clinician programmer. For example, the external controller 60 includes control circuitry 66 similar to the control circuitry 88 in the clinician programmer 70 and may similarly be programmed with external controller software stored in device memory.

Figure 6:
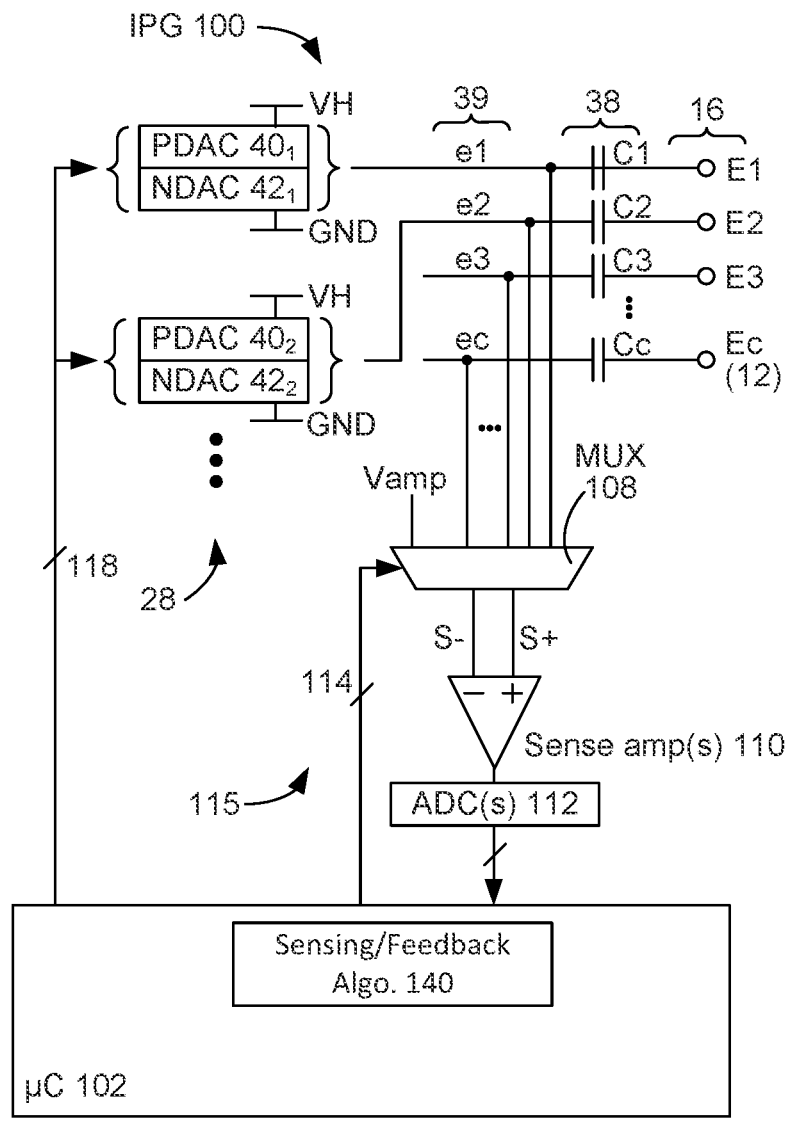
FIG. 6 illustrates sensing circuitry useable in an IPG.

An increasingly interesting development in pulse generator systems is the addition of sensing capability to complement the stimulation that such systems provide. FIG. 6 shows an IPG 100 that includes stimulation and sensing functionality. (An ETS as described earlier could also include stimulation and sensing capabilities). FIG. 6 shows further details of the circuitry in an IPG 100 that can provide stimulation and sensing innate or evoked signals. The IPG 100 includes control circuitry 102, which may comprise a microcontroller, such as Part Number MSP430, manufactured by Texas Instruments, Inc., which is described in data sheets at http://www.ti.com/microcontrollers/msp430-ultra-low-power-mcus/overview.html, which are incorporated herein by reference. Other types of controller circuitry may be used in lieu of a microcontroller as well, such as microprocessors, FPGAs, DSPs, or combinations of these, etc. Control circuitry 102 may also be formed in whole or in part in one or more Application Specific Integrated Circuits (ASICs), such as those described and incorporated earlier. The control circuitry 102 may be configured with one or more sensing/feedback algorithms 140 that are configured to cause the IPG to make certain adjustments and/or take certain actions based on the sensed neural signals.

The IPG 100 also includes stimulation circuitry 28 to produce stimulation at the electrodes 16, which may comprise the stimulation circuitry 28 shown earlier (FIG. 3). A bus 118 provides digital control signals from the control circuitry 102 to one or more PDACs $40_i$ or NDACs $42_i$ to produce currents or voltages of prescribed amplitudes (I) for the stimulation pulses, and with the correct timing (PW, F) at selected electrodes. As noted earlier, the DACs can be powered between a compliance voltage VH and ground. As also noted earlier, but not shown in FIG. 4, switch matrices could intervene between the PDACs and the electrode nodes 39, and between the NDACs and the electrode nodes 39, to route their outputs to one or more of the electrodes, including the conductive case electrode 12 (Ec). Control signals for switch matrices, if present, may also be carried by bus 118. Notice that the current paths to the electrodes 16 include the DC-blocking capacitors 38 described earlier, which provide safety by preventing the inadvertent supply of DC current to an electrode and to a patient's tissue. Passive recovery switches $41_i$ (FIG. 3) could also be present but are not shown in FIG. 6 for simplicity.

IPG 100 also includes sensing circuitry 115, and one or more of the electrodes 16 can be used to sense innate or evoked electrical signals, e.g., biopotentials from the patient's tissue. In this regard, each electrode node 39 can further be coupled to a sense amp circuit 110. Under control by bus 114, a multiplexer 108 can select one or more electrodes to operate as sensing electrodes (S+, S−) by coupling the electrode(s) to the sense amps circuit 110 at a given time, as explained further below. Although only one multiplexer 108 and sense amp circuit 110 are shown in FIG. 6, there could be more than one. For example, there can be four multiplexer 108/sense amp circuit 110 pairs each operable within one of four timing channels supported by the IPG 100 to provide stimulation. The sensed signals output by the sense amp circuitry are preferably converted to digital signals by one or more Analog-to-Digital converters (ADC(s)) 112, which may sample the output of the sense amp circuit 110 at 50 kHz for example. The ADC(s) 112 may also reside within the control circuitry 102, particularly if the control circuitry 102 has A/D inputs. Multiplexer 108 can also provide a fixed reference voltage, Vamp, to the sense amp circuit 110, as is useful in a single-ended sensing mode (i.e., to set S− to Vamp).

So as not to bypass the safety provided by the DC-blocking capacitors 38, the inputs to the sense amp circuitry 110 are preferably taken from the electrode nodes 39. However, the DC-blocking capacitors 38 will pass AC signal components (while blocking DC components), and thus AC components within the signals being sensed will still readily be sensed by the sense amp circuitry 110. In other examples, signals may be sensed directly at the electrodes 16 without passage through intervening capacitors 38.

According to some embodiments, it may be preferred to sense signals differentially, and in this regard, the sense amp circuitry 110 comprises a differential amplifier receiving the sensed signal S+ (e.g., E3) at its non-inverting input and the sensing reference S− (e.g., E1) at its inverting input. As one skilled in the art understands, the differential amplifier will subtract S− from S+ at its output, and so will cancel out any common mode voltage from both inputs. This can be useful for example when sensing various neural signals, as it may be useful to subtract the relatively large-scale stimulation artifact from the measurement (as much as possible). Examples of sense amp circuitry 110, and manner in which such circuitry can be used, can be found in U.S. Patent Application Publications 2019/0299006, 2020/0305744, 2020/0305745 and 2022/0233866.

Figure 7:
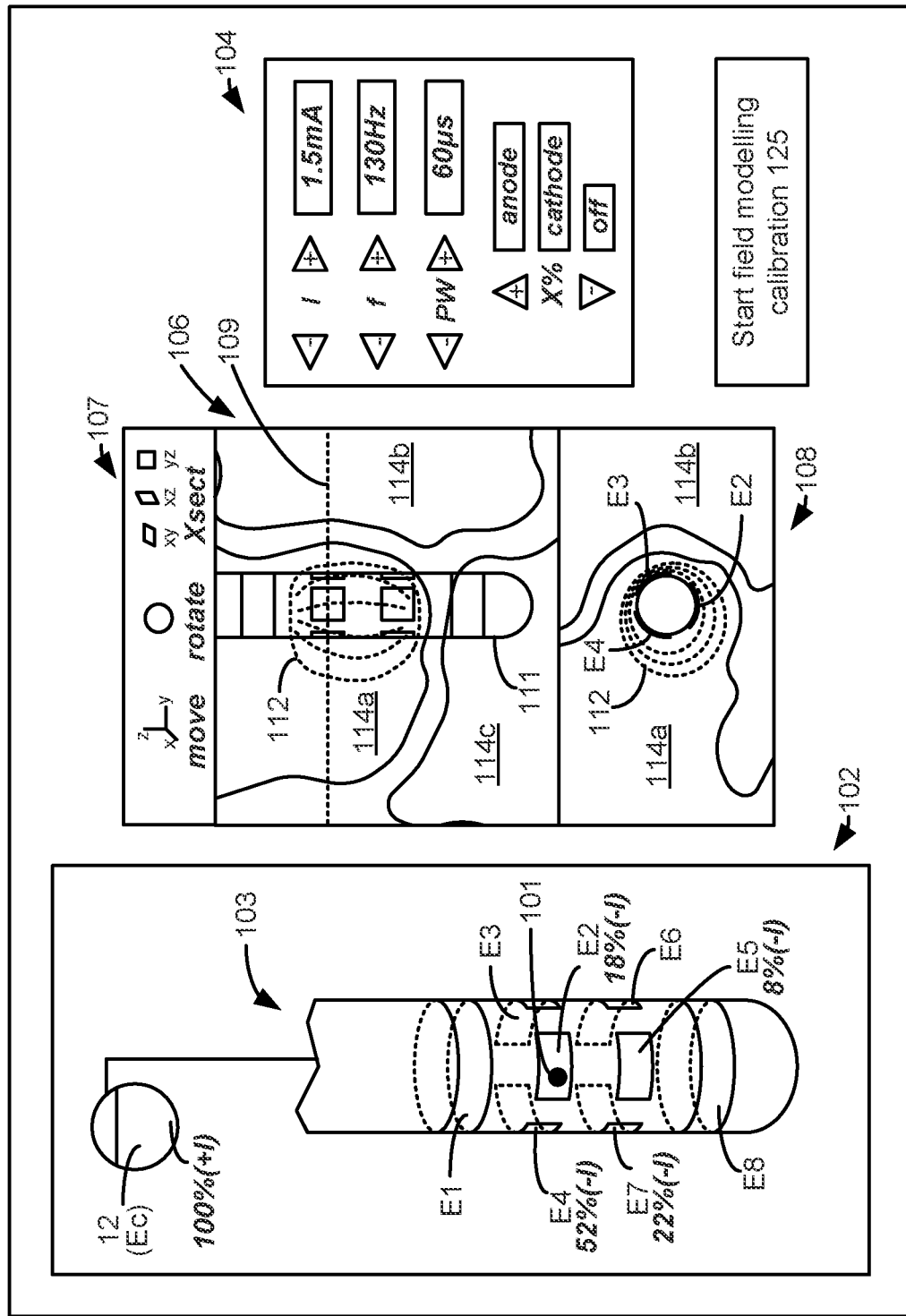
FIG. 7 illustrates an embodiment of a user interface (UI) for programming stimulation.

Particularly in the DBS context, it can be useful to provide a clinician with a visual indication of how stimulation selected for a patient will interact with the tissue in which the electrodes are implanted. This is illustrated in FIG. 7, which shows a Graphical User Interface (GUI) 100 operable on an external device capable of communicating with an IPG 110 or ETS 150. Typically, and as assumed in the description that follows, GUI 100 would be rendered on a clinician programmer 70 (FIG. 5), which may be used during surgical implantation of the leads, or after implantation when a therapeutically useful stimulation program is being chosen for a patient. However, GUI 100 could be rendered on a patient external programmer 60 (FIG. 5) or any other external device capable of communicating with the IPG 110 or ETS 150.

GUI 100 allows a clinician (or patient) to select the stimulation program that the IPG 110 or ETS 150 will provide and provides options that control sensing of innate or evoked responses, as described below. In this regard, the GUI 100 may include a stimulation parameter interface 104 where various aspects of the stimulation program can be selected or adjusted. For example, interface 104 allows a user to select the amplitude (e.g., a current I) for stimulation; the frequency (f) of stimulation pulses; and the pulse width (PW) of the stimulation pulses. Stimulation parameter interface 104 can be significantly more complicated, particularly if the IPG 100 or ETS 150 supports the provision of stimulation that is more complicated than a repeating sequence of pulses. See, e.g., U.S. Patent Application Publication 2018/0071513. Nonetheless, interface 104 is simply shown for simplicity in FIG. 7 as allowing only for amplitude, frequency, and pulse width adjustment. Stimulation parameter interface 104 may include inputs to allow a user to select whether stimulation will be provided using biphasic (FIG. 2A) or monophasic pulses, and to select whether passive charge recovery will be used, although again these details aren't shown for simplicity.

Stimulation parameter interface 104 may further allow a user to select the active electrodes—i.e., the electrodes that will receive the prescribed pulses. Selection of the active electrodes can occur in conjunction with a leads interface 102, which can include an image 103 of the one or more leads that have been implanted in the patient. Although not shown, the leads interface 102 can include a selection to access a library of relevant images 103 of the types of leads that may be implanted in different patients.

In the example shown in FIG. 7, the leads interface 102 shows an image 103 of a single split-ring lead 33 like that described earlier with respect to FIG. 1B. The leads interface 102 can include a cursor 101 that the user can move (e.g., using a mouse connected to the clinician programmer 70) to select an illustrated electrode 16 (e.g., E1-E8, or the case electrode Ec). Once an electrode has been selected, the stimulation parameter interface 104 can be used to designate the selected electrode as an anode that will source current to the tissue, or as a cathode that will sink current from the tissue. Further, the stimulation parameter interface 104 allows the amount of the total anodic or cathodic current +I or −I that each selected electrode will receive to be specified in terms of a percentage, X. For example, in FIG. 7, the case electrode 12 Ec is specified to receive X=100% of the current I as an anodic current +I. The corresponding cathodic current −I is split between electrodes E2 (0.18*−I), E4 (0.52*−I), E5 (0.08*−I), and E7 (0.22*−I). Thus, two or more electrodes can be chosen to act as anodes or cathodes at a given time using MICC (as described above), allowing the electric field in the tissue to be shaped. The currents so specified at the selected electrodes can be those provided during a first pulse phase (if biphasic pulses are used), or during an only pulse phase (if monophasic pulses are used).

GUI 100 can further include a visualization interface 106 that can allow a user to view an indication of the effects of stimulation, such as electric field image 112 formed on the one or more leads given the selected stimulation parameters. The electric field image 112 is formed by field modelling in the clinician programmer 70. Only one lead is shown in the visualization interface 106 for simplicity, although again a given patient might be implanted with more than one lead. Visualization interface 106 provides an image 111 of the lead(s) which may be three-dimensional.

The visualization interface 106 preferably, but not necessarily, further includes tissue imaging information 114 taken from the patient, represented as three different tissue structures 114*a*, 114*b* and 114*c* in FIG. 7 for the patient in question, which tissue structures may comprise different areas of the brain for example. Such tissue imaging information may comprise a Magnetic Resonance Image (MRI), a Computed Tomography (CT) image or other type of image and is preferably taken prior to implantation of the lead(s) in the patient. Often, one or more images, such as an MRI, CT, and/or a brain atlas are scaled and combined in a single image model. As one skilled in the art will understand, the location of the lead(s) can be precisely referenced to the tissue structures 114*i* because the lead(s) are implanted using a stereotactic frame (not shown). This allows the clinician programmer 70 on which GUI 100 is rendered to overlay the lead image 111 and the electric field image 112 with the tissue imaging information in the visualization interface 106 so that the position of the electric field 112 relative to the various tissue structures 114*i* can be visualized. The image of the patient's tissue may also be taken after implantation of the lead(s), or tissue imaging information may comprise a generic image pulled from a library which is not specific to the patient in question.

The various images shown in the visualization interface 106 (i.e., the lead image 111, the electric field image 112, and the tissue structures 114*i*) can be three-dimensional in nature, and hence may be rendered in the visualization interface 106 in a manner to allow such three-dimensionality to be better appreciated by the user, such as by shading or coloring the images, etc. Additionally, a view adjustment interface 107 may allow the user to move or rotate the images, using cursor 101 for example.

GUI 100 can further include a cross-section interface 108 to allow the various images to be seen in a two-dimensional cross section. Specifically, cross-section interface 108 shows a particular cross section 109 taken perpendicularly to the lead image 111 and through split-ring electrodes E2, E3, and E4. This cross section 109 can also be shown in the visualization interface 106, and the view adjustment interface 107 can include controls to allow the user to specify the plane of the cross section 109 (e.g., in XY, XZ, or YZ planes) and to move its location in the image. Once the location and orientation of the cross section 109 is defined, the cross-section interface 108 can show additional details. For example, the electric field image 112 can show equipotential lines allowing the user to get a sense of the strength and reach of the electric field at different locations. Although GUI 100 includes stimulation definition (102, 104) and imaging (108, 106) in a single screen of the GUI, these aspects can also be separated as part of the GUI 100 and made accessible through various menu selections, etc.

It has been observed that DBS stimulation in certain positions in the brain can evoke neural responses, i.e., electrical activity from neural elements, which may be measured. One example of such neural responses are resonant neural responses, referred to herein as evoked resonant neural responses (ERNAs). See, e.g., Sinclair, et al., "Subthalamic Nucleus Deep Brain Stimulation Evokes Resonant Neural Activity," Ann. Neurol. 83(5), 1027-31, 2018. The ERNA responses typically have an oscillation frequency of about 200 to about 500 Hz. Stimulation of the STN, and particularly of the dorsal subregion of the STN, has been observed to evoke strong ERNA responses, whereas stimulation of the posterior subthalamic area (PSA) does not evoke such responses. Thus, ERNA can provide a biomarker for electrode location, which can potentially indicate acceptable or perhaps optimal lead placement and/or stimulation field placement for achieving the desired therapeutic response.

Figure 8:
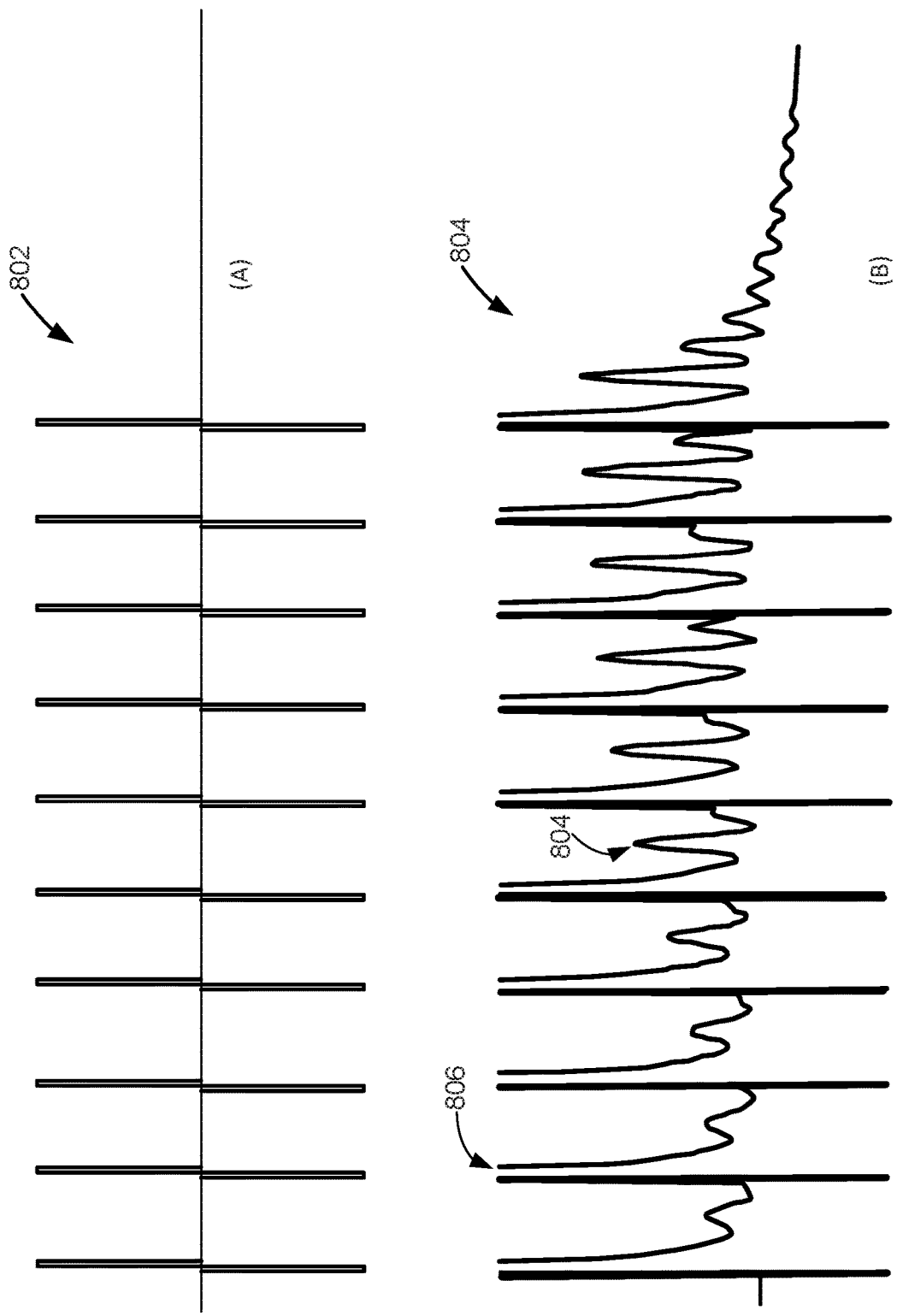
FIG. 8 illustrates evoked resonant neural activity (ERNA).

FIG. 8 illustrates an example of an ERNA response to a burst of ten symmetric monopolar biphasic pulses 802. The stimulation waveform 802 is illustrated as trace (A) and the recorded response 804 is illustrated as trace (B). The recorded response comprises stimulation artifacts 806 immediately following each stimulation pulse. The form of these stimulation artifacts may depend on the evoking stimulation. According to some embodiments, the stimulation artifacts may be removed or suppressed at various stages in the sensing chain. The recorded response may also contain an evoked compound action potential (ECAP) occurring 1-2 milliseconds after the stimulation pulse, though the ECAP in trace (B) is obscured by the stimulation artifact. The ERNA responses 804 build following each pulse. Notice that the amplitude of the oscillating ERNA response 804 increases during the burst and then persists even after the stimulation ceases. The ERNA response may in some embodiments be enhanced by periods where stimulation is withheld.

Figure 9:
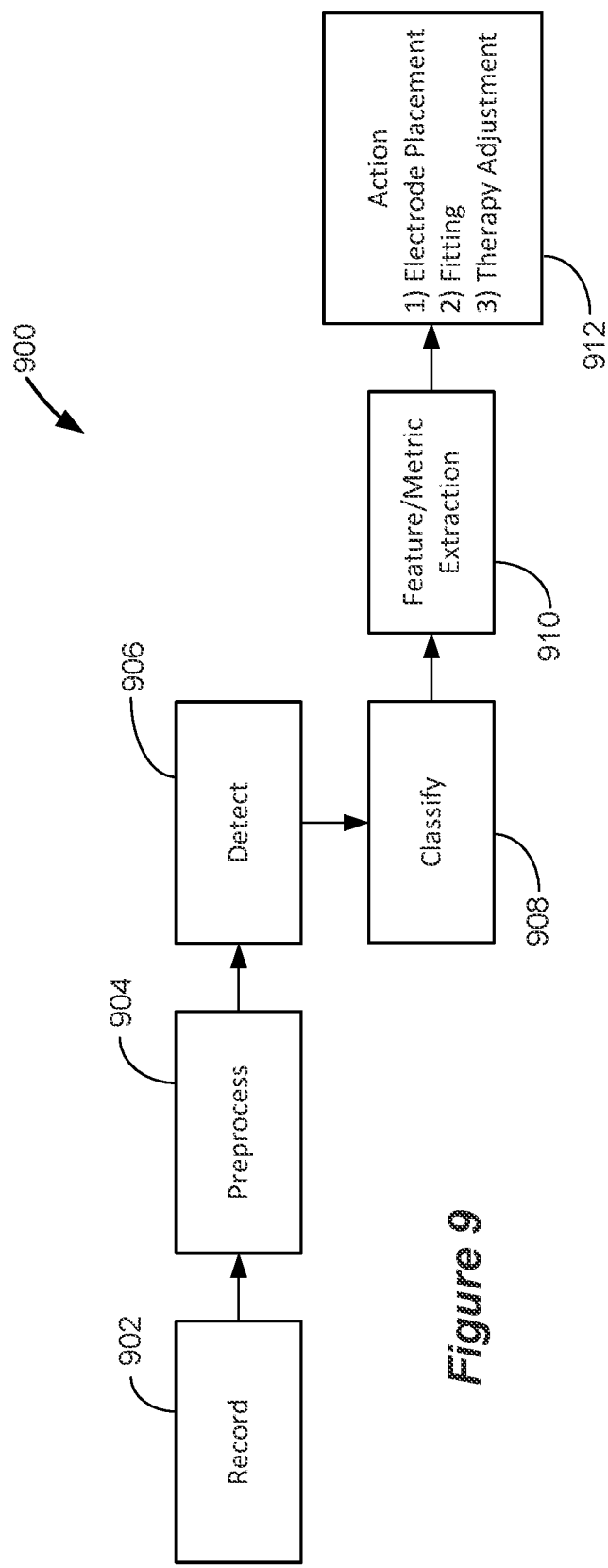
FIG. 9 illustrates a workflow for using recorded neural responses to inform aspects of DBS therapy.

This disclosure particularly relates to methods and systems for using recorded neural activity as a biomarker to inform aspects of neuromodulation therapy, such as DB S therapy. FIG. 9 illustrates a generalized workflow 900, according to aspects of the disclosure. The illustrated workflow 900 is intended to provide a high-level overview; the various steps of the workflow are described in more detail below. According to the workflow 900, electrical activity (i.e., field potentials and the like) occurring at implanted electrodes may be recorded 902. Such recorded electrical activity may include evoked and/or innate neural activity, as well as other activity, such as stimulation artifacts. The recorded signal(s) may be preprocessed 904 to reduce noise, eliminate stimulation artifacts, and the like. Peaks (or other features) of the recorded signal or derivatives thereof may be detected 906 to determine if a signal of interest is present. The detected peaks or other features may be classified 908 to determine if they posses the right temporal or frequency characteristics (or other characteristics) to potentially serve as biomarkers that may be useful for informing aspects of therapy. If a given peak/feature does meet the criteria for serving as a biomarker, the peak/feature may be analyzed to extract certain features or metrics 910. Such features or metrics can serve as feedback to inform various actions 912 related to neuromodulation therapy. For example, changes in the feature/metric may tracked or the value of the feature/metric can be compared to threshold values to determine whether to take some action regarding the therapy. Stated differently, the determined features/metrics may be indicative of the therapeutic efficacy of the stimulation, which may be tied to aspects of stimulation, such as lead placement, stimulation placement, electrode configuration, stimulation parameters, and the like. Thus, the features/metrics may be used to direct actions related to those aspects.

Figure 10:
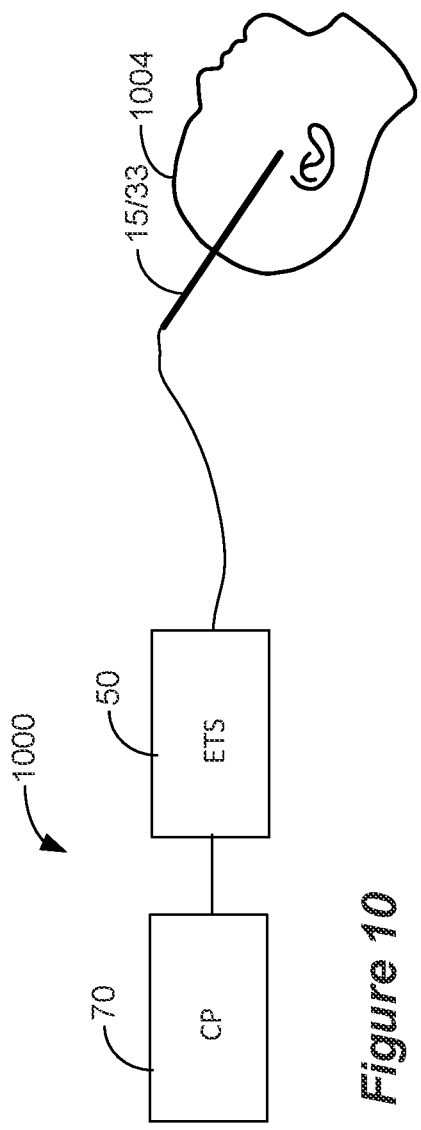
FIG. 10 illustrates a system for using recorded neural responses for surgical support during electrode lead implantation.

The workflow 900 may be used to inform various aspects related to neuromodulation therapy and therefore, certain actions 912 may be taken based on the measurements and analysis described herein. According to one embodiment, the workflow may be used to provide surgical support to direct lead placement during the implantation of the electrode(s) for providing DBS therapy. FIG. 10 illustrates a schematic of a system 1000 for performing implantation of an electrode lead (e.g., lead 15 or lead 33, FIGS. 1A/1B) in the brain of a patient 1004. The electrode lead may generally be any lead configured for DBS, for example micro-electrode recording leads, and especially those that include macro stimulation electrodes, especially directional. More electrodes on the lead can provide greater resolution. The electrode lead may comprise directional electrodes (such as the electrodes illustrated on lead 33 (FIG. 1B)). Greater resolution may also be provided by the ability to use MICC and current steering to provide stimulation locations that may be between the locations of actual physical electrodes.

The system 1000 also comprises one or more devices for controlling the stimulation and sensing provided at the electrode lead. The illustrated embodiment comprises a clinician programmer (CP) 70 for programming the stimulation and sensing parameters. The functionality of a CP 70 may be like that described above (FIG. 5), for example. The CP used during lead implantation may be the same machine or a different machine as the one used to program the patient's IPG later, during the fitting procedure. The clinician can use the CP 70 to select the electrodes of the lead 15/33 that will be used to provide stimulation, the parameters of the stimulation waveform(s) that will be applied, and the electrode(s) that will be used to sense evoked responses. In the illustrated system 1000, the CP 70 provides those selections to an ETS 50. The ETS 50 causes the stimulation to be applied to at leads. The ETS 50 also receives, and records sensed signals from the lead. The CP and ETS may communicate via a wired or a wireless connection. In the illustrated embodiment, a single ETS component is shown. However, according to some embodiments, multiple components could be used, for example, separate components for providing stimulation and for receiving and recording sensed signals. The CP may communicate with either or both ETS components in such an embodiment. According to some embodiments, aspects of the CP functionality and the ETS functionality may be combined in a single device. For example, the ETS 50 may itself be configured for programming the stimulation and/or sensing parameters. Alternatively, the functionality of receiving and recording the sensed signals (correlated with the stimulation configuration/parameters) may be embodied in the CP 70, for example as a module or subroutine additional to the CP functionality described above. Regardless of the exact configuration, the system is capable of causing stimulation of a defined waveform to be applied using selected one or more electrode on the lead, and of sensing/recording responses evoked by the stimulation. Further, the system 1000 (e.g., in either the CP 70 and/or the ETS 50) comprises control circuitry configured to perform the steps of the various algorithms and methods that are described below. The control circuitry may be so configured by executing program code stored on non-volatile computer-readable media.

Using a system 1000, as illustrating in FIG. 10, the clinician may seek to properly place the electrode lead (e.g., 15/33) at a position within the patient's brain to provide the optimum therapy. The system executes the workflow 900 (FIG. 9), and more specifically, the algorithms and methods described below to perform the classifications, to extract features/metrics from sensed and recorded neural activity and use those features/metrics as biomarkers to determine characteristics of electrode placement; including whether the lead is well placed, its location with respect to previously placements or measurements, among other characteristics.

According to some embodiments, the system 1000 may include a graphical user interface (GUI), which may display an indication of the sensed response data and the extracted features/metrics of the classified signals. The GUI may display (a) representation(s) of the lead(s) and correlations between the sensed signals, the stimulation parameters/locations, and the extracted features/metrics. According to some embodiments, the GUI may provide an indication of the likelihood that an electrode lead, in its present position, is likely to provide therapy that is good and robust, based on the features/metrics extracted from the classified signals. Such information is useful to inform the clinician's decision to leave the lead in its present position or to seek a better location. Such an indication may be based on historical data correlating one or more of the features/metrics with therapeutic efficacy, models based on historical data, or modeled data. Such data may be configured within a database, for example. If the extent of data is adequate, then the system may provide a quantitative prediction of efficacy. For example, the indication might provide a numerical value (such as a percentage value) that the present location of the lead will provide good therapy. Alternatively, the system may provide a binary (yes/no) indication of whether the lead placement is expected to provide high efficacy. The determination of whether the lead placement is satisfactory may be based on one or more threshold values for the extracted features/metrics derived from the database, for example. In some embodiments, if the lead placement is unsatisfactory or a different placement is determined to be or may be superior, the system may indicate which changes to placement may be recommended, including changes to depth along the existing trajectory, as well as changes in trajectory. In some embodiments, the system can report when it does not have the information to make any of the above classifications or recommendations.

The workflow 900 may also be used following implantation surgery to facilitate the fitting procedure to program the patient's IPG for providing optimum therapy. For example, the extracted features/metrics from sensed, recorded, and classified neural activity may be used as biomarkers to inform the best electrodes for providing optimal stimulation and may inform the optimal stimulation parameters, such as stimulation amplitude, pulse width, frequency, patterns, and the like. In this embodiment, the clinician uses a CP 70 (FIG. 5) to communicate with the patient's IPG 10 to cause the IPG to issue various candidate stimulation waveforms. Responses to the stimulation may be recorded, pre-processed, and classified and features/metrics extracted from the classified neural responses may be used to guide programming of the IPG. Again, the extracted features/metrics may be compared to historical data correlating the feature/metric values with therapeutic efficacy to derive the best stimulation parameters. Additionally (or alternatively), patient feedback may be used to correlate the extracted features/metrics to therapeutic settings that the patient describes as being effective.

The IPG 10 and/or the CP 70 may be configured to perform aspects of the workflow 900. For example, aspects of the workflow and the methods and algorithms described below may be embodied in the microcontroller 102 of the IPG 10 (FIG. 6), for example, as aspects of the sensing/feedback algorithms 140. Aspects of the workflow and algorithms may be performed by the CP 70. The workflow 900 may also be used during the patient's ongoing therapy to periodically adjust stimulation parameters using the extracted features/metrics of the measured neural responses as a feedback variable. For example, the IPG may be programmed with one or more closed-loop feedback algorithms, such as Kalman filtering algorithms, heuristic algorithms, single or multiple threshold models, proportional-integral-derivative (PID) controller models, and the like. The control algorithm(s) may be used to control one or more stimulation parameters, such as current amplitude, frequency, pulse width, stimulation fractionalization, duty cycle, and the like, based on the features/metrics extracted from classified neural signals during ongoing therapy.

According to some embodiments, the workflow 900 is used to detect, classify, and analyze (i.e., extract features/metrics from) evoked (or innate) neural responses that are oscillating and decaying, such as the ERNA responses described above. However, it should be noted that other modalities of neural responses may be sensed and analyzed using the described methods.

Referring again to the workflow 900, the recording 902 of the electrical activity may occur while stimulation is being provided to the patient or shortly after stimulation has ceased. For example, according to some embodiments, stimulation may be provided using one or more of the electrodes of the electrode lead and the electrical activity may be recorded at one or more of the electrodes. MICC and current fractionalization, as described above, can be used to precisely control the stimulation location(s). Without precise control of stimulation (as provided by MICC/current fractionalization), the vector location of the peak response may be misinterpreted, unknown, or uncertain. Impedance measurements or other properties of the recorded response may be used to compensate for such uncertainties when using single source systems (i.e., systems without MICC/current fractionalization). However, MICC is preferred in these embodiments. According to some embodiments, stimulation is provided at one of the electrodes on the lead and recordings are made using one or two of the other electrodes, for example, the electrodes flanking the stimulating electrode. According to other embodiments, stimulation is provided at one electrode and recordings are acquired at most or all the other electrodes on the lead. In embodiments wherein multiple electrode leads are implanted, stimulation and recording may occur on different leads. In still other embodiments, such as the coordinated reset (CR) embodiments described below, stimulation may be provided at two or more electrodes to stimulate different sub-populations of neural elements. In such embodiments, recordings may be acquired at multiple recording electrodes.

Figure 11A:
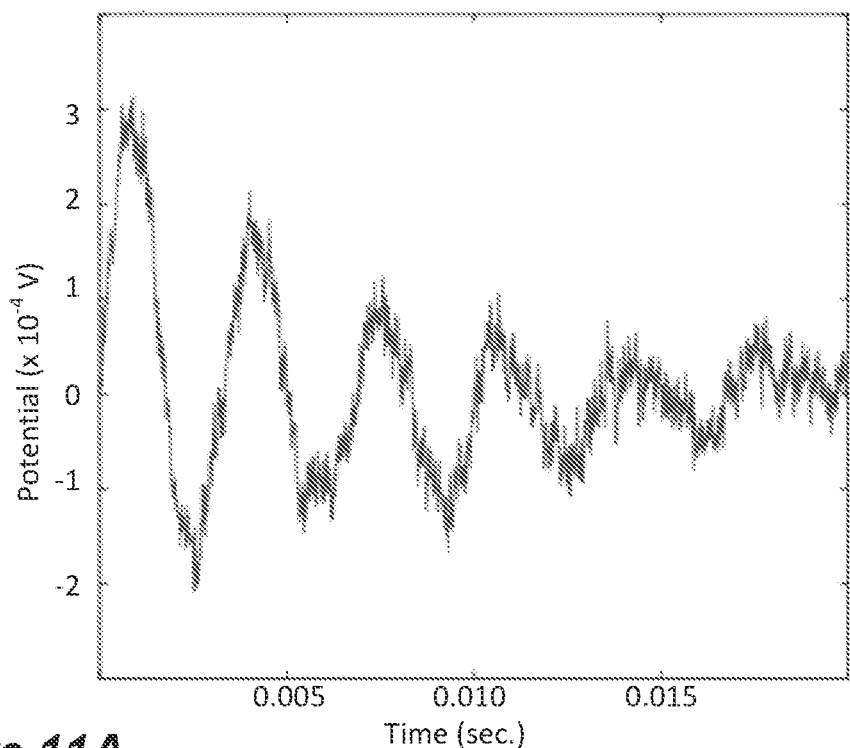
FIGS. 11A and 11B illustrate preprocessing of a decaying oscillatory neural response signal.
Figure 11B:
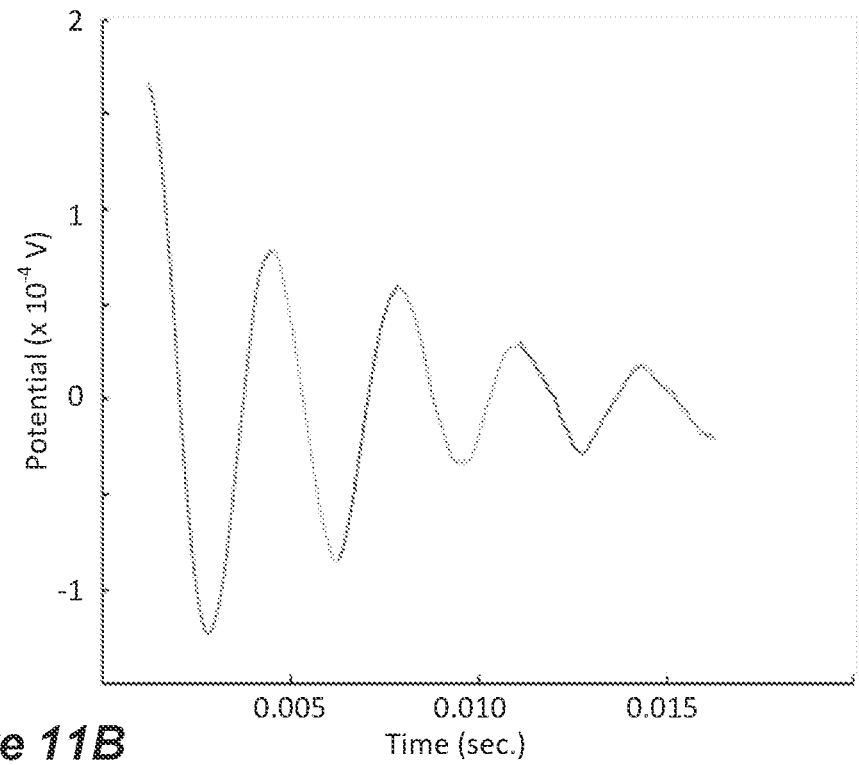

Signal filtering techniques may be used to select a time window of interest for recording the signals. For example, the right hand limit of the window of interest may be selected, especially by determining when the signal has decayed to a desirable minimum. The signals recorded at the sensing electrode(s) may be preprocessed. The processing may involve sampling the signals. Ideally, the sampling rate will be at a frequency that is at least twice the frequency of any feature of interest in the signal. However, if that sampling rate is not possible, then sampling techniques, such as compressed sensing may be used in situations where the expected wave form of the neural signal is known ahead of time. For example, if it is known that the neural signal of interest is expected to be a decaying oscillating signal, such as the ERNA responses discussed above, compressed sensing may be used to reconstruct the signal. Note that the compressed sensing techniques may be applied to signals that are not decaying/oscillating. If a stimulation artifact is present the signal may be cropped or filtered to remove the stimulation artifact. Also, the signal may be filtered using a low pass filter to remove high frequency noise, or averaged to remove other types of noise. According to some embodiments, the low pass filter may have a cutoff of about 600 Hz. FIG. 11A illustrates a recording from an electrode. FIG. 11B illustrates the signal resulting from preprocessing the signal to remove the contribution from the stimulation artifact and smoothing high frequency noise with a low pass filter.

Once the recordings from the sensing electrode(s) are preprocessed, the preprocessed signal may be analyzed to detect peaks or other features of interest in the recorded signal. The detecting may involve extracting one or more extrema (i.e., peaks or troughs) larger than a minimum prominence threshold. For example, peaks with a prominence of at least 0.1× the maximum signal may be extracted. The time and amplitude of each of the extracted peaks may be recorded.

Once signal features meeting the threshold criteria are detected and extracted, they may be classified to determine if they have the right characteristics to be considered as biomarkers, i.e., neural features of interest. Signal features not meeting the classification criteria may be rejected (i.e., not treated as informatory). The classification may be based on one or more criteria of the extracted signal. For example, the signal may be classified according to one or more of the following criteria:

Threshold number of peaks within a timeframe/window: According to some embodiments, the number of peaks (and valleys) of the signal may be determined and the signal may be classified (i.e., treated as informatory) only if that number exceeds a defined threshold, for example, at least two peaks and two valleys. Other threshold values for the number of peaks/valleys may be defined, depending on the implementation.

Amplitude Threshold: According to some embodiments, the signal may be classified only if one or more peaks (or valleys) have an absolute amplitude that exceeds a defined threshold. For example, the signal may be classified only if the signal has at least one peak and at least one valley having an absolute amplitude of at least 20 microvolts. Other threshold amplitude values may be defined, depending on the implementation. It should be noted here that amplitude can mean the raw signal, the signal after some pre-processing (esp. filtering), and especially the signal normalized, e.g. by all recorded channels, by the maximum from a set of recordings, against background noise (e.g. as a ratio of noise floor or lower-level), or the like.

Frequency/Temporal Parameters: According to some embodiments, the signal may be classified only if the signal has a frequency corresponding to the expected neurological response. For example, according to some embodiments, the signal may be classified only if the first three or more intervals have a frequency of 200-500 Hz. According to some embodiments, the signal may be classified only if the intervals are consistent. For example, the signal may be classified only if the first three or more intervals are within 20% of each other. Moreover, according to some embodiments, the signal may be classified if the decay exceeds a defined time threshold, for example greater than 3 milliseconds.

Signals classified according to one or more of the above criteria may be analyzed to extract one or more features or metrics from the signal to serve as a biomarker (i.e., feedback variable) to inform actions related to the patient's therapy. The extracted features or metrics may be the same as those used to perform the classification. For example, the extracted feature(s)/metric(s) may be one or more of the peak amplitudes, the number of peaks, the frequency, the decay time, etc.

The above discussion relates to detecting and classifying signals of interest using time domain processing. The signals recorded at the sensing electrodes can also be analyzed in the frequency domain. According to some embodiments, the sensed signal is processed using a fast Fourier transform (FFT) to convert the time domain signal to the frequency domain. The spectral characteristics of various peaks in the frequency domain signal can be classified to determine if they correspond to a signal that can be used as a biomarker. According to some embodiments, classifying the frequency domain signal involves determining the relative band power of the signal that occurs in a frequency of interest, for example, in a frequency corresponding to a neural signal, such as the ERNA responses discussed above.

Figure 12A:
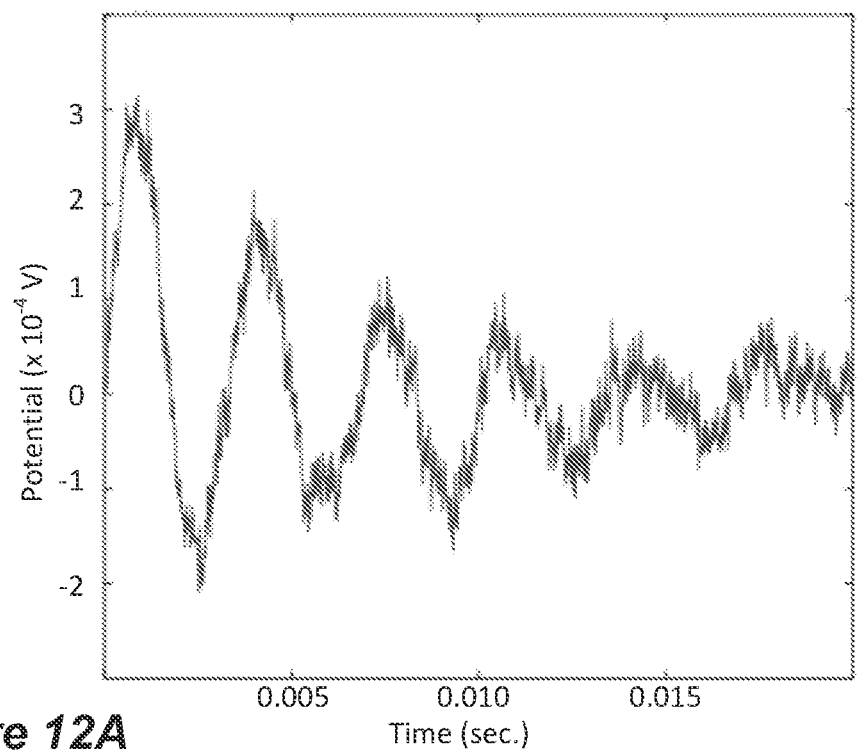
FIGS. 12A and 12B illustrate processing of a decaying oscillatory neural response signal in the frequency domain.
Figure 12B:
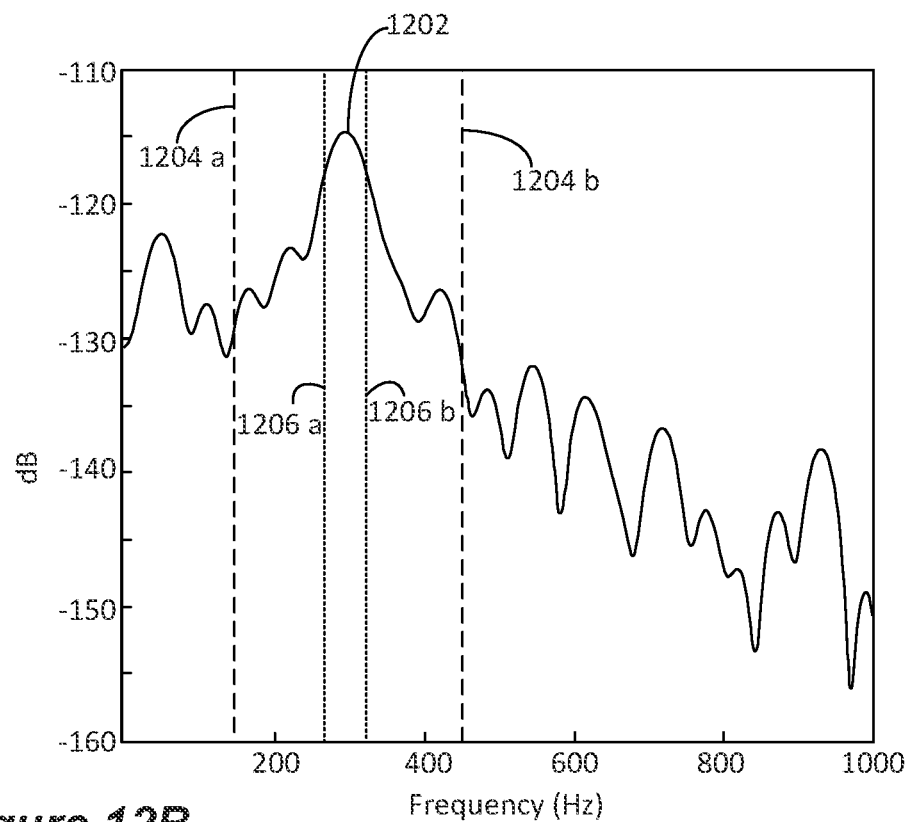

FIG. 12A illustrates a recording from an electrode. FIG. 12B shows the result of converting the time domain electrode recording to the frequency domain. The frequency spectrum shows a prominent peak 1202 at about 300 Hz. The dashed lines 1204a and 1204b demarcate the frequency range where particular neural responses are expected to occur. In the illustrated embodiment, that frequency range is 150-450 Hz, which corresponds to the frequency range of expected ERNA responses. Other frequency ranges corresponding to other neural responses could be chosen, for example, 200-600 Hz, 100-400 Hz, or 225-300 Hz. The dotted lines 1206a and 1206b demarcate the full width at half max of the 300 Hz peak. To classify whether the 300 Hz peak should be considered as indicative of a particular neural response of interest, the ratio of the power within the range of 150-450 Hz relative to the power in the overall spectrum (0-1000 Hz) can be compared to a predefined threshold value. According to some embodiments, the power within the range of the FWHM of the peak relative to the power of the overall power, and/or relative to the power within the frequencies of interest (i.e., 150-450 Hz) can be used to classify the peak. Other characteristics of the peak, such as the FWHM (which is proportional to the decay constant for a decaying oscillating signal, such as an ERNA signal) can also be used to classify the peak.

Figure 13:
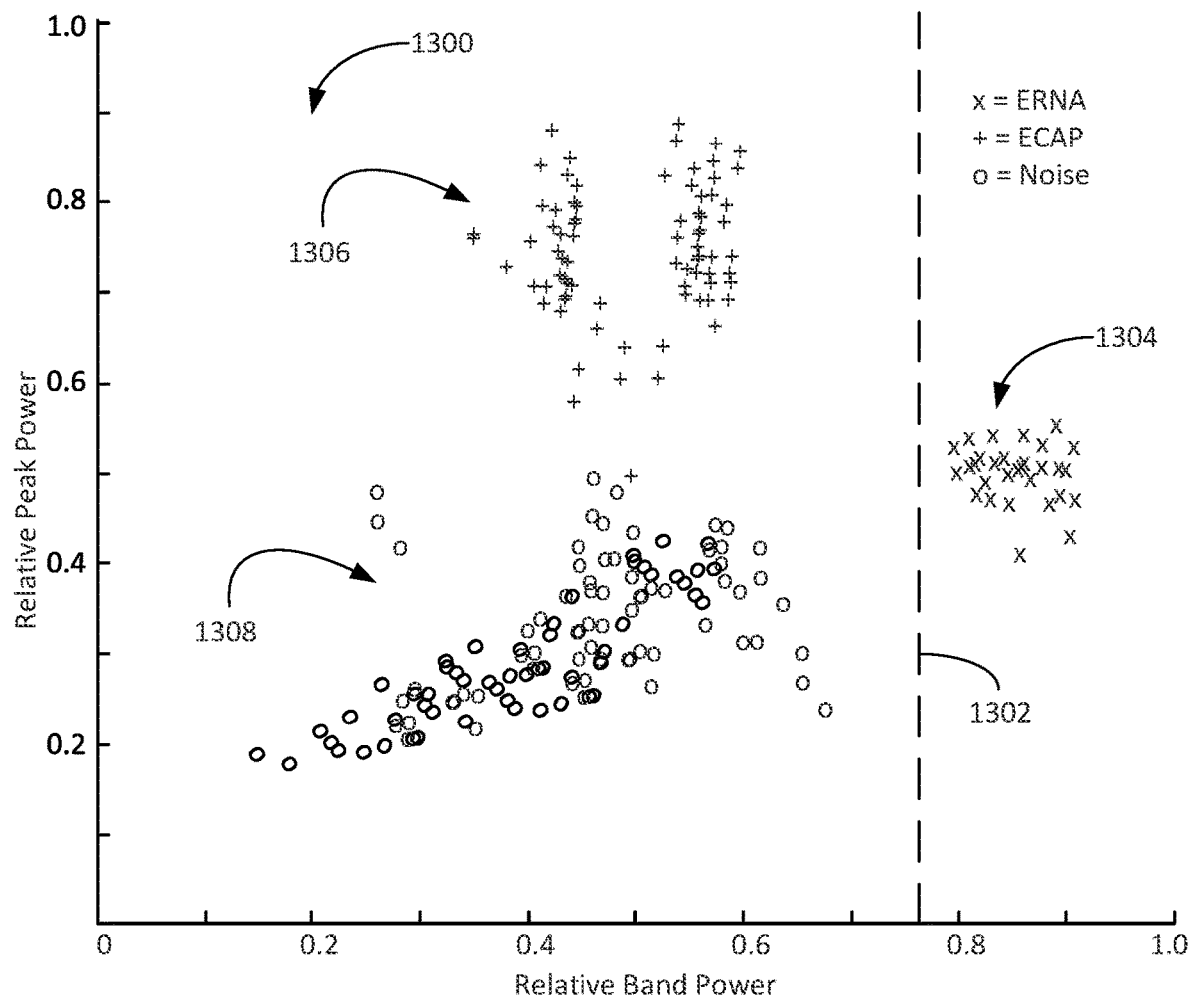
FIG. 13 illustrates an example of classifying frequency domain peaks based on relative band power.

FIG. 13 illustrates one example of how frequency domain peaks can be classified. FIG. 13 shows a scatter plot 1300 of multiple peaks obtained from spectrographs (for example, extracted from multiple electrode recordings). The horizontal axis represents the relative band power, i.e., the power in the spectral region where a neural signal is expected (for example, 150-450 Hz) relative to the power in the overall spectrum (0-1000 Hz). The vertical axis represents the relative peak power, i.e., the power in the spectral region corresponding to the FWHM of the peak relative to the power in the region where a neural signal is expected (for example, 150-450 Hz). The plot includes a band power threshold 1302 at about 0.75 (represented as a dashed line). If a spectrum contains a peak in the region where a neural signal is expected (e.g., 150-450 HZ) and the spectrum has a relative band power in that region exceeding the band power threshold, then the peak is classified as being a relevant neural signal. In the illustrated plot, peaks 1304 (represented by x's) are classified as corresponding to a relevant neural signal (in this case, ERNA signals). Other peaks, such as peaks 1306 derived from ECAPs (represented by +'s) and 1308 derived from noise (represented by o's) are not classified as relevant neural signals. It should be noted that in the scatter plot 1300, the classification is based only on the relative band power. However, other (or additional) criteria may be used. For example, peaks may also be classified based on the relative peak power. According to some embodiments, the method may use a first threshold for the relative band power and a second threshold for the relative peak power such that only peaks that exceed both of those thresholds are classified. The peaks may also be classified based on their FWHM, which is proportional to the decay constant of a decaying sinusoidal signal, whereby only peaks corresponding to a signal with a significantly long decay are classified. Peaks may be classified based on their confidence interval, as described in more detail below. In general, the disclosed methods involve using predetermined criteria believed to correspond to a relevant neural signal, analyzing the frequency domain signal to determine if those criteria are met, and classifying the signal as an actionable signal only if those criteria are met.

As mentioned above, once an actionable neural signal is classified, the signal may be analyzed to extract one or more features or metrics from the signal to serve as a biomarker (i.e., feedback variable) to inform actions related to the patient's therapy. The extracted features or metrics may be the same as those used to perform the classification. Examples of features or metrics may include the relative band power, the relative peak power, the FWHM, the decay constant, etc. According to some embodiments, the classification of the neural signal may be performed in the frequency domain and the extraction of features or metrics to use as biomarkers may be performed on the time domain signal to provide metrics such as peak amplitude, the number of peaks, the decay time, etc. A combination of features of the signal in the time domain and/or the frequency domain may be used as a fingerprint of a useful neural response.

As described above, the ratio of power in a frequency band of interest relative to the overall power can be used to classify signals to determine if they contain an actionable neural response. The discussion mentioned that an FFT may be used to perform the requisite power calculations. However, other processing steps may be used for processing the recorded signals. For example, the recorded signals may be multiplied by a smoothing function, such as a windowing or tapering function, prior to taking the FFT. Examples of such functions include Hann functions, Hanning functions, Hamming functions, Prolate spheroidal sequences, etc., as are known in the art.

Embodiments of the disclosure relate to classifying decaying oscillating neural signals, such as the ERNA responses described above. Since the signal is decaying, noise may eventually mask the low amplitude portion of the signal. To prevent this, according to some embodiments the recorded signal may be multiplied with an exponentially rising function, referred to as a matched filter function, prior to computing the FFT. Ideally, the matched filter function rises at the same rate as the decay rate of the neural signal. According to some embodiments, the rising function can be optimized by first performing an initial set of trials to compute the raw FFT transformed function. The width of the raw FFT spectrum may be used to estimate a putative decay rate. For a decaying sinusoid with a decay rate described by $e^{-t/\tau}$, the width of the spectrum is $1/\pi\tau$. Once the value of $\tau$ is determined, subsequent recorded signals may be multiplied by matched filter function $e^{t/\tau}$ prior to computing the FFT. Even if the decay of the raw signal is not described by a perfectly exponential form, using this method may enhance the signal to noise ratio (SNR). Another approach for accounting for noise and spectral leakage of decaying sinusoidal functions is to multiply the recorded signal by multiple tapering functions optimally chosen to enhance the SNR, as described in Multiple-taper spectral analysis of terrestrial free oscillations: part I, Park, et al., Geophys. J. Roy. Astr. Soc., (1987) 91, 755-94.

According to some embodiments, the presence of a neural signal can be determined using a least squares method. Let X(t) denote a recorded signal putatively containing a decaying oscillating neural signal, such as an ERNA response. A model for X(t) can be defined as $X(t)=A(t) \sin(2\pi ft+\phi)+\epsilon(t)$, where $A(t) \sin(2\pi ft+\phi)$ describes the neural signal and $\epsilon(t)$ is the residual term (i.e., the background in the absence of the neural signal). If $A(t)=a\, e^{-t/\tau}$, i.e., for a decaying oscillating neural signal, such as an ERNA response, the unknown parameter a can be determined using least squares regression in the frequency domain. If A(t) is found to be nonzero for a frequency in the range where the neural signal is expected, then one can say that a neural signal is present; otherwise one can say that a neural signal is not present. Notably, the least squares method described here does not simply compute power in the relevant frequency range as a means of confirming the presence of a neural signal. Even if the power in the band is high, A(t) will still be zero if a neural signal is not present. If A(t) is not well described by a simple exponential fall off, the frequency domain regression can be generalized to include corrections to an exponential fall off.

According to some embodiments, the recorded signals are processed to determine a confidence for the detection of a neural signal. This is useful because a high amount of power in the frequency range where a neural signal is expected to occur is not necessarily an indication that the neural signal is present. One method of determining confidence may comprise determining a first confidence interval around a region of the spectrum when (or where) a neural signal is not expected to occur and determining a second confidence interval around a region of the spectrum when (or where) a neural signal is expected to occur. If the confidence intervals do not overlap, then the presence of the neural signal can be declared. For example, data can first be obtained in the absence of stimulation and the spectrum can be estimated using multiple snippets of such data. Then multiple snippets of data can be obtained that putatively includes the neural signal. A confidence interval (e.g., a 95% confidence interval) can be computed around both estimates. The presence of a neural signal can be declared when: (1) the power in the frequency band where a neural signal is expected to occur exceeds the power outside of that band, and (2) the confidence intervals of the two estimates do not overlap in that frequency range. Note that this confidence test focuses only on power. For decaying oscillating neural signals, such as ERNA responses, further confidence testing may involve recording a signal that putatively contains a decaying oscillating neural signal, performing the regression described above, and performing an F-test for the significance of the regression coefficient, for example, as described in Park et al., referenced above. If the signal at the putative neural response frequency exceeds the confidence interval, then that indicates that the signal at that frequency has a significant sinusoidal decay. The presence of the neural signal can be classified as being present if the amplitude of the putative neural signal is significantly above the 95% confidence level for the F-distribution. According to some embodiments, the prediction confidence (i.e., 95% or 99%, etc.) required to classify a signal as comprising a neural response can be adjusted, for example, depending on what type of action is being taken based on the neural response. For actions that may not be considered critical, a lower confidence (e.g., 95%) may be used. Such non-critical actions may comprise making minor adjustments to stimulation parameters, for example. More critical actions, such as turning off stimulation, might require a higher confidence (e.g., 99%).

Figure 14:
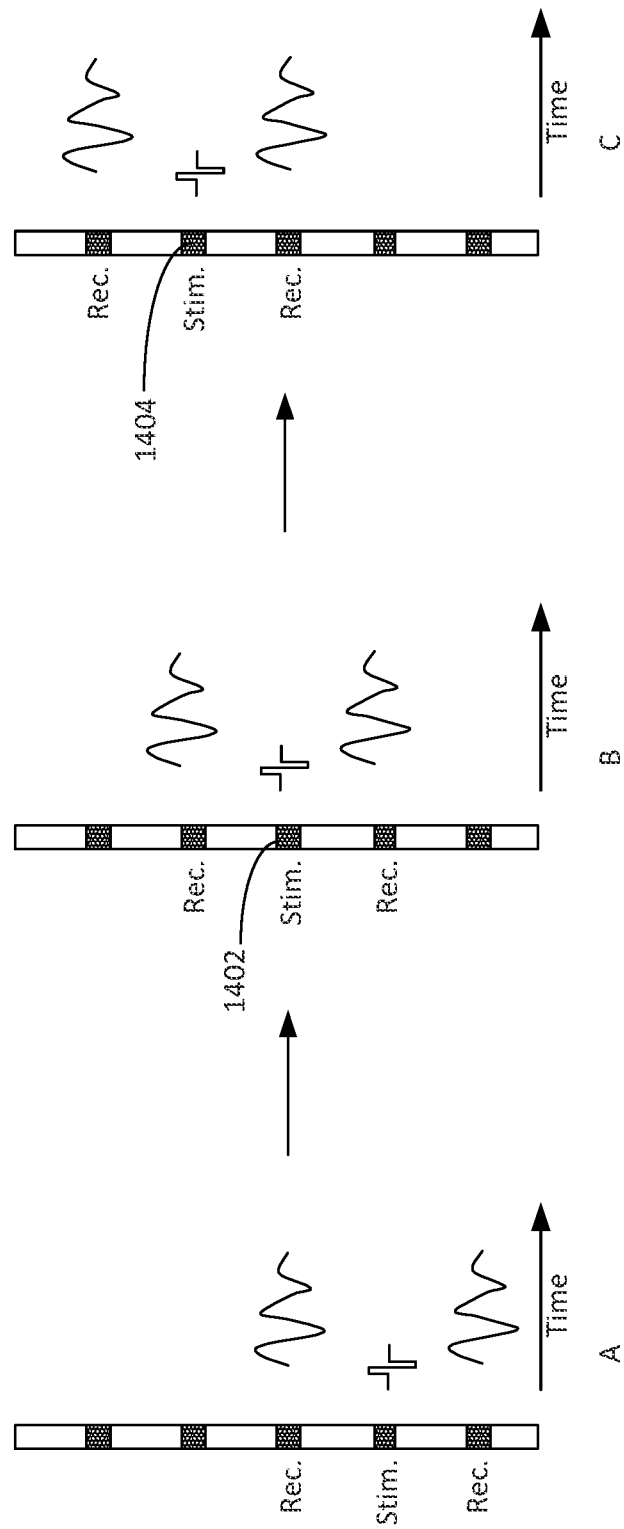
FIG. 14 illustrates sequential stimulating and recording at multiple positions on an electrode lead.

According to some embodiments, the multiple electrodes may be used as the recording electrodes. For example, a stimulating electrode flanked by two symmetrically placed recording electrodes may be used, as illustrated in FIG. 14. According to some embodiments, the signals recorded at the recording electrodes may be processed and classified, and features/metrics may be determined for them using any of the techniques described above. Different locations of the stimulating and recording electrodes may be used, as shown in the configurations A, B, and C in the illustration, to determine the location along the lead that provides the best neural response signal, i.e., a neural response "sweet spot." Appreciate that the sweet spot may occur at some position between the physical electrodes. Thus, according to some embodiments, the process may be further refined by fractionating the current between stimulating electrodes to produce a virtual electrode closer to the sweet spot. For example, assume that the configuration A provides a weak neural response, whereas configurations B and C provide stronger neural responses. It may be hypothesized that the true sweet spot is at a location between electrodes 1402 and 1404. A better stimulation location may be found by fitting a smooth function to the location-response data and using current fractionalization to move the effective stimulation location toward the maximum of the smooth function. Stimulation may be applied at a virtual electrode position between electrodes 1402 and 1404 and a recording can be made. The process may be iteratively repeated until an optimum stimulation location is determined. Note that other stimulation and recording electrodes may be used to carry out this process. For example, according to one embodiment, the top and bottom electrodes of the lead may be used for recording and the stimulation position may be moved up and down the lead using the remaining electrodes.

Figure 15:
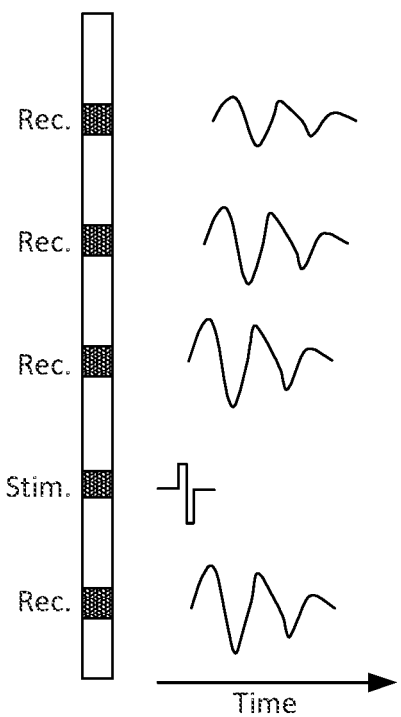
FIG. 15 illustrates stimulating at one position and recording at multiple positions on an electrode lead.

As shown in FIG. 15, stimulation may be provided at one of the electrodes and all the other electrodes may be used for recording. Note that the illustrated lead only contains five electrodes (for simplicity of illustration), but the lead may comprise more electrodes that are not illustrated. The signals recorded at the different electrodes may have different amplitudes, delays, and phases. Dimensionality reduction techniques, such as principal component analysis, singular value decomposition, independent component analysis, etc., may be used to separate the signal components of interest containing the neural response from other signal components, such as noise and the stimulation artifact. The classification and extraction techniques described above can then be used to analyze the extracted interesting signal components. The resulting components and their contributions may provide a "fingerprint" of the recording montage for the stimulation electrode. Iteration over the stimulation electrodes can be used to determine the electrode(s) at which stimulation results in the most desirable neural response signal fingerprint. Machine learning or other statistical techniques may be used to infer current fractionalization parameters that will elicit the strongest neural response fingerprint. Reconstitution or scaling factors may be used to correct for known differences between the recording electrodes, for example, if electrodes are of a different type, such as ring electrodes and segmented electrodes, if electrodes have different impedance values, and/or if electrodes are different distances away from the evoking electrode.

Figure 16:
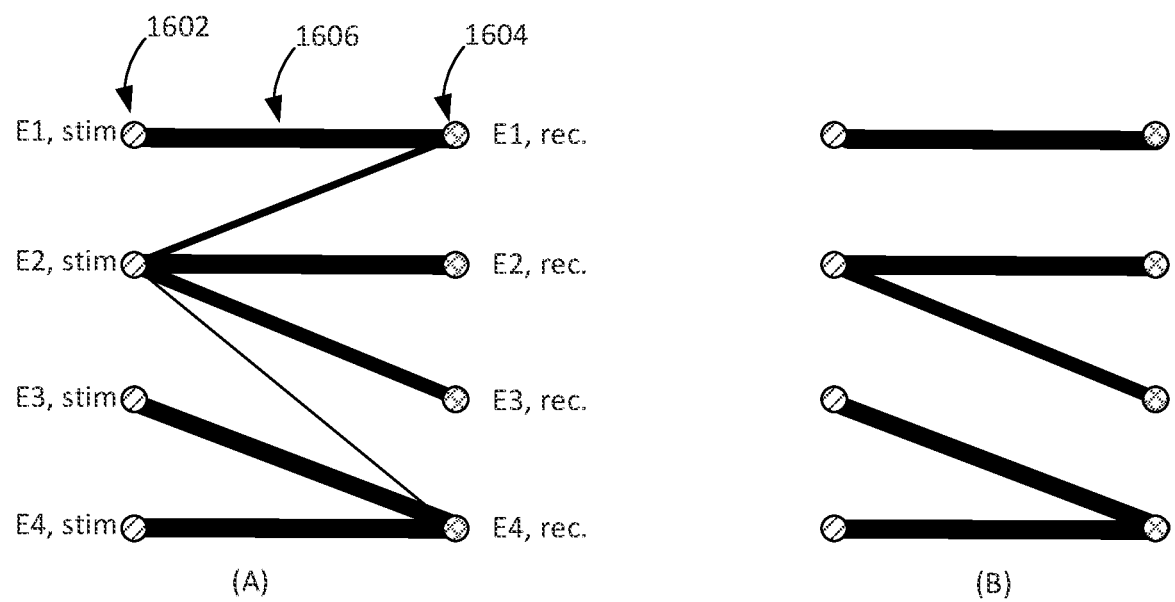
FIG. 16 illustrates graphical analysis of recorded neural response signals.

According to some embodiments, the stimulating montage can be extended to include all the electrodes of the array. Graphical analysis can be used to elucidate coupling between the various stimulating and recording electrodes. FIG. 16 illustrates an embodiment wherein each of the electrodes are used for stimulation and a single neural response feature, such as amplitude for example, is determined at each of the electrodes. The stimulating electrodes are depicted on the left vertices 1602 and the recording electrodes are depicted on the right vertices 1604. Each of the stimulating electrodes is joined to each recording electrode with an edge 1606, the weight (width) of which is proportional to the extracted neural response. Referring to FIG. 16(A), stimulation at E1 results in a strong neural response only at E1 itself. Stimulation at E2 results in a strong neural response at E2, a weaker neural response at E3, and a still weaker neural response at E1. A weighted graph, such as FIG. 16A may be considered one example of a multi-dimensional neural response fingerprint.

Graph-theoretic analysis techniques may be used to reduce the connectivity of the graph (e.g. reduce a fully connected graph into disconnected components). One example of such a technique is to discard edges with a weight less than a predetermined threshold to break the graph into disjoined islands, as shown in FIG. 16B. The disconnected graph, as shown in FIG. 16B, may be considered as another example of a multi-dimensional neural response fingerprint. According to some embodiments, more than one neural response features can be used to characterize the neural response, in which case, multiple graphs, such as A and/or B may be constructed and the combination of graphs may be considered as the multi-dimensional neural response fingerprint.

The multi-dimensional (i.e., multi-electrode) fingerprints, as described, can be used to determine which fields (i.e., which electrodes) to use for providing therapy. For example, each electrode may be chosen as a field with an amplitude selected based on its average weight of the neural response elicited by that electrode. Alternatively, each electrode may be chosen as a field with an amplitude based on the average neural signal recorded at the electrode when the other electrodes are used as stimulating electrodes. Alternatively, each isolated island (FIG. 16B) may be taken as a field with either a constant amplitude or an amplitude equaling the average neural response weight within the island. Moreover, fractionalization current within an island can be related to the neural response weights of the individual weights within that island.

Neural responses recorded at multiple recording locations and elicited by stimulation at multiple stimulation locations may be accumulated to provide multi-electrode neural response fingerprints. Neural responses recorded at a given recording electrode (for multiple stimulation locations) and/or elicited by a given stimulation location (and recorded at multiple recording locations) can be thought of as an image where one dimension is the stimulating/recording electrode and another dimension is time. A full dataset can be thought of as a stack of images. These images can be compressed using image compression techniques, such as jpeg, for example. Using a few components of the compressed image allows recovery of most of the image while discarding the noise. The data may also be thought of as a three-dimensional data cube with one dimension being time and the remaining two dimensions being the stimulating and recording electrodes. In such embodiments, generalizations of various decomposition techniques, such as Singular Value Decomposition and/or Independent Components Analysis from matrices to tensors may be used to split the data into its most prominent components. Such decompositions may be considered as fingerprints of the neural responses. A desirable neural response may comprise a pattern of independent components and this pattern may be utilized to guide electrode placement or to monitor the efficacy of therapy.

Thus far, the disclosure has been concerned with using aspects of recorded neural response signals as biomarkers for informing aspects of neuromodulation therapy. The above disclosure explains how to record electrical activity and to classify the recorded electrical activity that potentially includes valuable biomarker information that can be used to direct aspects of therapy. The electrical activity may be recorded and analyzed in the time domain, the frequency domain, or in a mixture of both. Multiple electrodes may be used as the stimulating electrode and/or the recording electrode. The dimensionality reduction techniques described above may be used to derive neural response fingerprints, which may be correlated to therapeutic effectiveness. For example, the neural response fingerprints may be correlated to indicators, such as unified Parkinson's disease rating (UPDRS) scores, or the like. Thus, the neural response fingerprints may serve as feedback criteria for optimizing a patient's therapy.

Oscillatory neural signals, such as the decaying oscillatory ERNA responses discussed above, are believed to be emergent from connectivity between neural elements. Therefore, such neural responses may serve as biomarkers in the context of network modulatory neurostimulation, where the efficacy of the stimulation may depend on how the stimulation changes the underlying neural networks.

It has been hypothesized that a cause of symptoms (e.g., tremors) in DBS patients relates to an undue high degree of neural synchronicity (hyper-synchronicity) in the target neural population. That is, the neurons within a target location are overly coupled to one another, and thus fire in synch, leading to symptoms. Further, a neural population may also have an unduly low degree of neural synchronicity (hypo-synchronicity), which may also lead to symptoms.

Figure 17B:
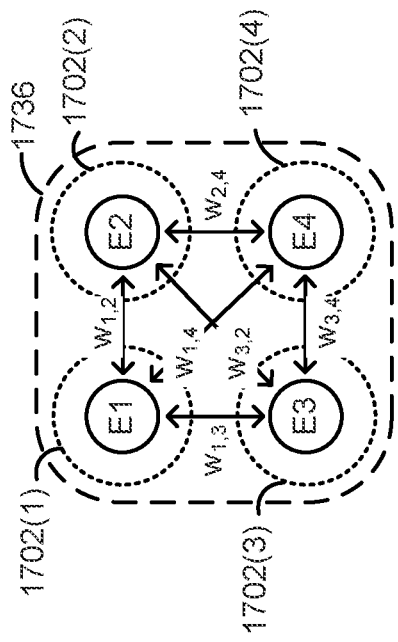
FIGS. 17A and 17B illustrate aspects of coordinated reset stimulation.
Figure 17A:
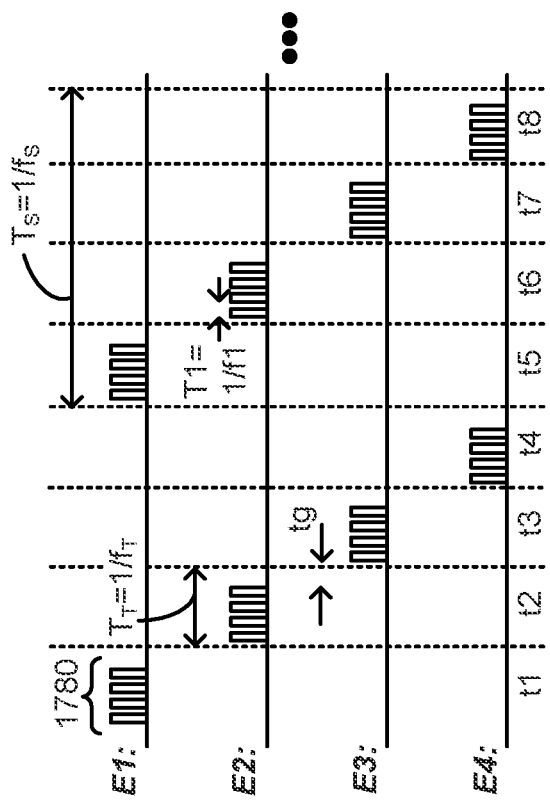

A technique that may alter the synchronicity of neural firing in the target neural population, called coordinated reset, is shown in FIG. 17A. It should be noted that while coordinated reset is discussed herein as a specific example of multi-site temporally complex stimulation sequences, the techniques described herein can be extended to other modalities. For example, one can deliver bursts of stimulation to multiple sites without a defined temporal relationships so that each burst is independent. At the other extreme, one can stimulate with precisely chosen timings between bursts either at different electrode sets on a single lead or across multiple leads. Roughly one can think of coordinated reset as being in between these two extremes.

Coordinated reset involves using stimulation pulses at two or more electrodes Ex to stimulate different sub-populations $1702(x)$ of neurons within the target neural population 1736 at different times, as shown in FIG. 17B. For example, a first packet of pulses 1780 is issued from electrode E1 during a time period t1, with the goal of causing neurons within subpopulation 1702(1) to fire. Another packet of pulses 1780 is issued from electrode E2 during a later time period t2, with the goal of causing neural elements (e.g., neurons, fibers, nerve terminals, etc.) within sub-population 1702(2) to fire, and so on for electrodes E3 and E4 and sub-populations 1702(3) and 1702(4) during times t3 and t4. The pulse packets 1780 can then be repeated at electrodes E1-E4 during times periods t5-t8 as shown in FIG. 17A. A gap in time may exist between successive pulse packets 1780. Further, the pulse packets 1780 delivered to electrodes E1-E4 occur during a time period Ts, which preferably matches the frequency fs at which the sub-populations $1702(x)$ are noticed to oscillate, such as between 12 to 25 Hz for example.

FIG. 17B shows a generalized map which explains the degree of coupling between neural sub-populations $1702(x)$ within the target neural population 1736. Coupling can be explained by denoting a weight of coupling $w_{x,y}$ between two sub-populations $1702(x)$ and $1702(y)$ proximate to electrodes Ex and Ey. (Electrodes E1-E4 may be on the same or on different leads 18, 20). When target neural tissue 1736 is hyper-synchronized, the weights are too high; if hypo-synchronized, the weights are too low. Thus, when target neural tissue 1736 is hyper-synchronized, firing of neurons in say sub-population 1702(1) causes too easily the firing of neurons in sub-population 1702(3), even if firing of these sub-populations 1702(1) and 1702(3) occurs at different times or phases. High neural coupling between sub-populations, even if not at the same phase, is described as "entrainment." Likewise, when target neural tissue 1736 is hypo-synchronized, firing of neurons in say sub-population 1702 (1) may not readily cause the firing of neurons in sub-population 1702(3), even if it should.

Coordinated reset as provided by the pulse packets 1780 of FIG. 17A may cause the phase of the oscillatory neural activity in the sub-populations $1702(x)$ to be reset. For example, the time period between pulse packets, $T_T$, may be 12.5 msec. Suppose that when sub-population 1702(1) fires, sub-population 1702(2) will naturally fire due to high entrainment ($w_{1,2}$) 15 msec later when no stimulation is present. Because the pulse packet 1780 at electrode E2 is issued earlier than this—at 12.5 msec—the natural coupling between sub-populations 1702(1) and 1702(2) is disrupted and therefore reset. In other words, issuing the pulse packets 1780 during time periods t1, t2, t3, etc., is likely to disrupt the otherwise naturally high coupling and phase of firing between the sub-populations $1702(x)$ were stimulation not used, which promotes desynchronization and assists in the reduction of symptoms. By the same token, coordinate reset as described in FIG. 17A may also assist in synchronizing undesirably hypo-synchronized sub-populations $1702(x)$.

While coordinated reset is an interesting DBS programming paradigm, it faces challenges, such as how to determine which patients are likely to respond to coordinated reset, choosing which fields (i.e., electrodes) to use for providing stimulation, and choosing programming settings, including dosing, DBS frequency, coordinated reset frequency, and amplitude. These issues are particularly difficult in the context of coordinated reset paradigms, where the temporal aspect of efficacy is believed to differ from traditional DBS paradigms, which are not understood to change the underlying neural network. With traditional DBS, the effects of stimulation often manifest within seconds of applying stimulation. But since coordinated reset appears to effect neural networks over periods of hours or days, optimizing stimulation can be difficult. Accordingly, oscillatory neural responses, such as ERNA responses, which are emergent from the connectivity of neural sub-populations, offers particularly useful methods of elucidating changes within neural network promoted using coordinated reset therapy. In some cases, changes in the oscillatory neural responses may emerge before visible changes are detectable in the patient, providing emerging indications of health or disease before they are symptomatic.

According to some embodiments, recorded neural responses, such as the decaying oscillatory neural responses described above, may be used to predict if a patient is a candidate for coordinated reset therapy. Any of the techniques described above for classifying and extracting neural response metrics can be performed on the patient and the patient's neural response metrics (or fingerprints) can be compared to historical data for patients that have (or have not) responded well to coordinated reset stimulation to identify potential coordinated reset candidates.

As described above, coordinated reset settings are characterized by 1) a set of fields (i.e., electrodes) at which stimulation will be sequentially applied, and 2) a set of parameters (i.e., amplitudes, intra-burst rates, burst durations, and inter-burst times, etc.) for each of the fields. The techniques described above may be used to determine which electrodes are the best candidates to serve as fields for providing coordinated reset stimulation. For example, the techniques described herein can help identify sets of active electrodes that are related to each other via neural coupling strength. In particular, the multi-electrode techniques using dimensionality reduction and/or graphical analysis provide an indication of connectivity between the various electrodes, vis-à-vis the neural networks. Providing stimulation at multiple electrodes and recording at multiple electrodes and decomposing that information provides insight into the constituents in terms of the connectivity. According to some embodiments, electrodes that are determined to be highly coupled (e.g., the electrodes forming the disjoined islands of FIG. 16B) may be chosen as fields for coordinated reset. According to some embodiments, the best electrodes to use for coordinated reset may not necessarily be the electrodes that evoke the maximum response, but instead may be a set of electrodes that create similarly or sufficiently powerful response, and wherein an additional metric such as a distance metric between the electrodes is maximized. Such a distance metric may be based on the percentages of current allocated to each electrode in each field.

Having selected which electrodes to serve as fields for providing coordinated reset, the neural response analysis techniques described above can also inform parameter adjustment (i.e., adjustment of amplitudes, intra-burst rates, burst durations, and inter-burst times, etc.). As stimulation proceeds, the neural response fingerprint can be monitored to determine whether it is converging or diverging relative to an optimum neural response fingerprint, for example, in a closed loop manner. A closed loop feedback algorithm may adjust various aspects of the coordinated reset pattern to drive the neural response fingerprint toward the desired neural response outcome.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A medical device, comprising:
an implantable pulse generator (IPG) configured for implantation in a patient and comprising a plurality of electrode nodes, each electrode node configured to be coupled to an electrode configured to contact a patient's brain tissue; and
control circuitry configured to:
control stimulation circuitry to issue stimulation at a first one or more of the plurality of electrode nodes,
record an electrical signal at a second one or more of the plurality of electrode nodes,
classify the recorded electrical signal according to one or more classification criteria indicative of evoked resonant neural activity (ERNA) to determine if the recorded electrical signal contains ERNA,
if the recorded electrical signal does contain ERNA, extract one or more features of the ERNA,
adjust stimulation based on the one or more features, and
if the recorded electrical signal does not contain ERNA, make no adjustment based on the signal.

2. The device of claim 1, wherein the one or more classification criteria comprise one or more peaks or troughs with a prominence exceeding a predetermined threshold value or values.

3. The device of claim 1, wherein the one or more classification criteria comprise a number of peaks meeting or exceeding a predetermined threshold number of peaks within a predetermined time window.

4. The device of claim 1, wherein the one or more classification criteria comprise one or more peaks with amplitudes meeting or exceeding a predetermined amplitude threshold.

5. The device of claim 1, wherein the one or more classification criteria comprise one or more components within a range of predetermined frequencies and exceeding one or more predetermined thresholds.

6. The device of claim 1, wherein determining if the recorded electrical signal contains ERNA comprises assigning a confidence value that a neural response of interest is present and rejecting the recorded electrical signal unless the confidence value meets or exceeds a predetermined threshold.

7. The device of claim 1, wherein the one or more features of the ERNA comprises one or more of a band power, a peak power, a full width at half max (FWHM), or a decay constant.

8. The device of claim 1, wherein the one or more features of the ERNA comprises one or more of a peak amplitude or a number of peaks.

9. The device of claim 1, wherein the recorded electrical signal is a time domain signal, and wherein the control circuitry is configured to determine a frequency domain signal corresponding to the time domain signal.

10. The device of claim 9, wherein the step of classifying the electrical signal is performed on the frequency domain signal.

11. The device of claim 9, wherein the step of extracting one or more features of the ERNA is performed on the frequency domain signal.

12. The device of claim 10, wherein the step of extracting one or more features of the ERNA is performed on the time domain signal.

13. The device of claim 9, wherein determining if the recorded electrical signal contains ERNA further comprises determining if one or more relative band powers in one or more predetermined frequency ranges of the frequency domain signal meet or exceed one or more predetermined thresholds.

14. A method for providing stimulation to a patient's brain, wherein the patient is implanted with one or more electrode leads comprising a plurality of electrodes, the method comprising:
issuing stimulation at a first one or more of the plurality of electrodes,
recording an electrical signal at a second one or more of the plurality of electrodes,
classifying the recorded electrical signal according to one or more classification criteria indicative of evoked resonant neural activity (ERNA) to determine if the recorded electrical signal contains ERNA,
if the recorded electrical signal does contain ERNA, extract one or more features of the ERNA,
adjusting stimulation based on the one or more features, and
if the recorded electrical signal does not contain ERNA, making no adjustment based on the signal.

15. The method of claim 14, wherein the one or more classification criteria comprise one or more peaks or troughs with a prominence exceeding a predetermined threshold value or values.

16. The method of claim 14, wherein the one or more classification criteria comprise a number of peaks meeting or exceeding a predetermined threshold number of peaks within a predetermined time window.

17. The method of claim 14, wherein the one or more classification criteria comprise one or more peaks with amplitudes meeting or exceeding a predetermined amplitude threshold.

18. The method of claim 14, wherein the one or more classification criteria comprise one or more components within a range of predetermined frequencies and exceeding one or more predetermined thresholds.

19. The method of claim 14, wherein determining if the recorded electrical signal contains ERNA determining a frequency domain signal corresponding to the time domain signal.

20. The method of claim 19, wherein determining if the recorded electrical signal contains ERNA further comprises determining if one or more relative band powers in one or more predetermined frequency ranges of the frequency domain signal meet or exceed one or more predetermined thresholds.

\* \* \* \* \*